US008696122B2

(12) United States Patent
Hammer et al.

(10) Patent No.: US 8,696,122 B2
(45) Date of Patent: Apr. 15, 2014

(54) MULTI-FUNCTIONAL ADAPTIVE OPTICS RETINAL IMAGING

(75) Inventors: Daniel X. Hammer, Bedford, NH (US); R. Daniel Ferguson, Melrose, MA (US); Mircea Mujat, Acton, MA (US); Anket H. Patel, Methuen, MA (US); Nicusor V. Iftimia, Chelmsford, MA (US); Stephen Burns, Bloomington, IN (US)

(73) Assignee: Physical Sciences, Inc., Andover, MA (US)

( * ) Notice: Subject to any disclaimer, the term of this patent is extended or adjusted under 35 U.S.C. 154(b) by 281 days.

(21) Appl. No.: 13/011,404

(22) Filed: Jan. 21, 2011

(65) Prior Publication Data

US 2011/0234978 A1    Sep. 29, 2011

Related U.S. Application Data

(60) Provisional application No. 61/297,128, filed on Jan. 21, 2010.

(51) Int. Cl.
*A61B 3/10* (2006.01)
*A61B 3/12* (2006.01)

(52) U.S. Cl.
CPC .................................... *A61B 3/1225* (2013.01)
USPC ............................. 351/205; 351/206; 351/221

(58) Field of Classification Search
CPC ..................................................... A61B 3/1225
USPC .................. 351/205, 206, 208, 210, 221, 246
See application file for complete search history.

(56) References Cited

U.S. PATENT DOCUMENTS

| 4,264,152 A | 4/1981 | Crane |
|---|---|---|
| 4,443,075 A | 4/1984 | Crane |

(Continued)

FOREIGN PATENT DOCUMENTS

| EP | 0 307 185 | 3/1989 |
|---|---|---|
| EP | 0 770 370 | 5/1997 |

(Continued)

OTHER PUBLICATIONS

Zou et al., "Wavefront-aberration sorting and correction for a dual-deformable-mirror adaptive-optics system," *Optics Letters*, vol. 33(22) (2008) pp. 2602-2604. (3 pgs.).

(Continued)

*Primary Examiner* — Huy K Mai
(74) *Attorney, Agent, or Firm* — Proskauer Rose LLP

(57) ABSTRACT

An optical apparatus includes a system of optical components capable of operating in a scanning laser ophthalmoscope (SLO) mode and an optical coherence tomography (OCT) mode. The system of optical components includes a first optical module for the SLO mode, a second optical module for the OCT mode, and a first scanning device. The first optical module for the SLO mode includes a first source adapted to provide a first imaging beam for the SLO mode and a first detection device configured to receive a first signal associated with a first image of a retina of an eye. The second optical module for the OCT mode includes a second source adapted to provide a second imaging beam for the OCT mode and a second detection device configured to receive a second signal associated with a second image of the retina. The first scanning device is configured to move the first imaging beam along the retina in the slow axis of the SLO mode to acquire the first image and (ii) to move the second imaging beam along the retina in the fast axis of the OCT mode to acquire the second image.

26 Claims, 15 Drawing Sheets

(56) References Cited

U.S. PATENT DOCUMENTS

| | | |
|---|---|---|
| 4,561,436 A | 12/1985 | Munnerlyn |
| 4,569,354 A | 2/1986 | Shapiro et al. |
| 4,579,430 A | 4/1986 | Bille |
| 4,764,005 A | 8/1988 | Webb et al. |
| 4,765,730 A | 8/1988 | Webb |
| 4,768,873 A | 9/1988 | Webb |
| 4,768,874 A | 9/1988 | Webb et al. |
| 4,781,453 A | 11/1988 | Kobayashi |
| 4,856,891 A | 8/1989 | Pflibsen et al. |
| 4,881,808 A | 11/1989 | Bille et al. |
| 4,883,061 A | 11/1989 | Zeimer |
| 4,886,351 A | 12/1989 | Sabban et al. |
| 4,924,507 A | 5/1990 | Chao et al. |
| 4,931,053 A | 6/1990 | L'Esperance, Jr. |
| 4,964,717 A | 10/1990 | Koester |
| 5,029,220 A | 7/1991 | Juday |
| 5,094,523 A | 3/1992 | Reznichenko et al. |
| 5,098,426 A | 3/1992 | Sklar et al. |
| 5,106,184 A | 4/1992 | Milbocker |
| 5,122,135 A | 6/1992 | Dürr et al. |
| 5,129,400 A | 7/1992 | Makino et al. |
| 5,243,368 A | 9/1993 | Ito et al. |
| 5,252,999 A | 10/1993 | Sukigara et al. |
| 5,309,187 A | 5/1994 | Crossman et al. |
| 5,347,329 A | 9/1994 | Ota |
| 5,353,073 A | 10/1994 | Kobayashi |
| 5,360,010 A | 11/1994 | Applegate |
| 5,360,424 A | 11/1994 | Klopotek |
| 5,425,729 A | 6/1995 | Ishida et al. |
| 5,430,509 A | 7/1995 | Kobayashi |
| 5,437,274 A | 8/1995 | Khoobehi et al. |
| 5,480,396 A | 1/1996 | Simon et al. |
| 5,526,189 A | 6/1996 | Heacock |
| 5,673,097 A | 9/1997 | Heacock |
| 5,726,443 A | 3/1998 | Immega et al. |
| 5,767,941 A | 6/1998 | Ferguson |
| 5,777,719 A | 7/1998 | Williams et al. |
| 5,778,016 A | 7/1998 | Sucha et al. |
| 5,784,148 A | 7/1998 | Heacock |
| 5,861,938 A | 1/1999 | Heacock |
| 5,943,115 A | 8/1999 | Ferguson |
| 5,949,520 A | 9/1999 | Heacock |
| 5,976,502 A | 11/1999 | Khoobehi et al. |
| 6,027,216 A | 2/2000 | Guyton et al. |
| 6,099,127 A | 8/2000 | Manivannan et al. |
| 6,186,628 B1 | 2/2001 | Van de Velde |
| 6,195,202 B1 | 2/2001 | Kusunose |
| 6,199,986 B1 | 3/2001 | Williams et al. |
| 6,267,477 B1 | 7/2001 | Karpol et al. |
| 6,275,718 B1 | 8/2001 | Lempert |
| 6,299,311 B1 | 10/2001 | Williams et al. |
| 6,305,804 B1 | 10/2001 | Rice et al. |
| 6,331,059 B1 | 12/2001 | Kudryashov et al. |
| 6,379,006 B1 | 4/2002 | Eikelboom et al. |
| 6,471,691 B1 | 10/2002 | Kobayashi et al. |
| 6,582,079 B2 | 6/2003 | Levine |
| 6,758,564 B2 | 7/2004 | Ferguson |
| 6,890,076 B2 | 5/2005 | Roorda |
| 7,113,817 B1 | 9/2006 | Winchester et al. |
| 7,118,216 B2 | 10/2006 | Roorda |
| 7,284,862 B1 | 10/2007 | Lai et al. |
| 7,452,080 B2 | 11/2008 | Wiltberger et al. |
| 7,566,128 B2 | 7/2009 | Tsukada et al. |
| 7,794,081 B2 | 9/2010 | Fujishiro et al. |
| 8,025,402 B2 | 9/2011 | Ueno |
| 2003/0053026 A1 | 3/2003 | Roorda |
| 2003/0231285 A1 | 12/2003 | Ferguson |
| 2005/0012899 A1 | 1/2005 | Ferguson |
| 2005/0146784 A1 | 7/2005 | Vogt |
| 2005/0254008 A1 | 11/2005 | Ferguson et al. |
| 2007/0252951 A1 | 11/2007 | Hammer et al. |
| 2008/0088852 A1 | 4/2008 | Rogers et al. |
| 2011/0001927 A1* | 1/2011 | Kasper ............ 351/206 |

FOREIGN PATENT DOCUMENTS

| | | |
|---|---|---|
| JP | 06-261862 | 9/1994 |
| JP | 11-253403 | 9/1999 |
| JP | 2009-291252 | 12/2009 |
| WO | WO 90/09141 | 8/1990 |
| WO | WO 93/08877 | 5/1993 |
| WO | WO 95/28989 | 11/1995 |
| WO | WO 97/40405 | 10/1997 |
| WO | WO 03/105678 | 12/2003 |
| WO | WO 03/105679 | 12/2003 |
| WO | WO 2007/127291 A2 | 11/2007 |
| WO | 2008/039660 | 4/2008 |
| WO | 2009/059400 | 5/2009 |
| WO | WO 2009/095473 | 8/2009 |

OTHER PUBLICATIONS

America National Standards Institute, Inc. "American National Standard for Safe Use of Lasers" *Laser Institute of America*, (2000). (185 pgs.).

Alt et al., "Selective Targeting of The Retinal Pigment Epithelium Using an Acousto-Optic Laser Scanner," *Journal of Biomedical Optics*, vol. 10(6) (2005) pp. 064014-1-064014-11. (11 pgs.).

Bigelow et al., "Compact Multimodal Adaptive-Optics Spectral-Domain Optical Coherence Tomography Instrument for Retinal Imaging," *Journal of the Optical Society of America A*, vol. 24(5) (2007) pp. 1327-1336. (10 pgs.).

Cense et al., "In Vivo Depth-Resolved Birefringence Measurements of the Human Retinal Nerve Fiber Layer by Polarization-Sensitive Optical Coherence Tomography," *Optics Letters*, vol. 27(18) (2002) pp. 1610-1612. (3 pgs.).

Curcio et al., "Packing Geometry of Human Cone Photoreceptors: Variation With Eccentricity and Evidence for Local Anisotropy," *Visual Neuroscience*, vol. 9 (1992) pp. 169-180. (12 pgs.).

de Boer et al., "Improved Signal-to Noise Ratio in Spectral-Domain Compared with Time-Domain Optical Coherence Tomography," *Optics Letters*, vol. 28(21) (2003) pp. 2067-2069. (3 pgs.).

*Department of Defense Handbook*, "Laser Safety on Ranges and in Other Outdoor Areas," MIL-HDBK-828A, Appendix A: "Summary of Laser Safety Information for Fire Control Laser Systems," (1996) (136 pgs.).

Dreher et al., "Active Optical Depth Resolution Improvement of the Laser Tomographic Scanner," *Applied Optics*, vol. 28(4) (1989) pp. 804-808. (5 pgs.).

Drexler et al., "Enhanced Visualization of Macular Pathology With the Use of Ultrahigh-Resolution Optical Coherence Tomography," *Archives of Ophthalmology*, vol. 121 (2003) pp. 695-706. (12 pgs.).

Duncan et al., "High-Resolution Imaging with Adaptive Optics in Patients with Inherited Retinal Degeneration," *Investigative Ophthalmology & Visual Science*, vol. 48(7) (Jul. 2007) pp. 3283-3291. (9 pgs.).

Fercher et al., "Measurement of Intraocular Distances by Backscattering Spectral Interferometry," *Optics Communications*, vol. 117 (1995) pp. 43-48. (6 pgs.).

Fercher et al., "Optical Coherence Tomography—Principles and Applications," *Institute of Physics Publishing Reports on Progress in Physics*, vol. 66 (2003) pp. 239-303. (65 pgs.).

Ferguson et al., "A Line-Scanning Laser Ophthalmoscope (LSLO)," Abstract from *Investigative Ophthalmology & Visual Science*, (2003). (2 pgs.).

Ferguson et al., "Tracking Optical Coherence Tomography," *Optics Letters*, vol. 29(18) (2004) pp. 2139-2141. (3 pgs.).

Ferguson et al., "Wide-Field Retinal Hemodynamic Imaging With the Tracking Scanning Laser Ophthalmoscope," *Optics Express*, vol. 12(21) (2004) pp. 5198-5208. (11 pgs.).

Ferguson et al., "Tracking Adaptive Optics Scanning Laser Ophthalmoscope," *Proceedings of SPIE*, vol. 6138 (2006) pp. 613810-1-613810-9. (9 pgs.).

Gray et al, "In vivo Fluorescence Imaging of Primate Retinal Ganglion Cells and Retinal Pigment Epithelial Cell," *Optics Express*, vol. 14(16) (2006) pp. 7144-7158. (15 pgs.).

(56) References Cited

OTHER PUBLICATIONS

Hammer et al., "Foveal Fine Structure in Retinopathy of Prematurity: An Adaptive Optics Fourier Domain Optical Coherence Tomography Study," *Investigative Ophthalmology & Visual Science*, vol. 49(5) (2008) pp. 2061-2070. (10 pgs.).
Hammer et al, "Precision Targeting With a Tracking Adaptive Optics Scanning Laser Opthalmoscope,"*Presented at SPIE BIOS 2006 Advanced Biomedical and Clinical and Diagnostic Systems IV* (San Jose, CA), (Jan. 21-26, 2006), [online], [retrieved on Jul. 31, 2007]. Retrieved from the Internet <URL: http://www.psicorp.com/publications/PDF/sr-1256.pdf> (11 pgs.).
Hammer et al., "Active Retinal Tracker for Clinical Optical Coherence Tomography Systems," *Journal of Biomedical Optics*, in press. vol. 10(2) (2005) pp. 024038-1-024038-11. (11 pgs.).
Hammer et al., "Adaptive Optics Scanning Laser Ophthalmoscope for Stabilized Retinal Imaging," *Optics Express*, vol. 14(8) (2006) pp. 3354-3367. (13 pgs.).
Hammer et al., "Advanced Scanning Methods With Tracking Optical Coherence Tomography," *Optics Express*, vol. 13(20) (2005) pp. 7937-7947. (11 pgs.).
Hammer et al., "Compact Scanning Laser Ophthalmoscope With High-Speed Retinal Tracker," *Applied Optics*, vol. 42(22) (2003) pp. 4621-4632. (12 pgs.).
Hammer et al., "Hand-Held Digital Line-Scanning Laser Ophthalmoscope (LSLO)," *Proceedings of SPIE*, vol. 5314 (2004) pp. 161-169. (9 pgs.).
Hammer et al., "High Resolution Retinal Imaging With a Compact Adaptive Optics Spectral Domain Optical Coherence Tomography System," *Proceedings of SPIE*, vol. 6426 (2007) pp. 64261Q-1-64261Q-10. (10 pgs.).
Hammer et al., "Image Stabilization for Scanning Laser Ophthalmoscopy," *Optics Express*, vol. 10(26) (2002) pp. 1542-1549. (8 pgs.).
Hammer et al., "Line-Scanning Laser Ophthalmoscope," *Journal of Biomedical Optics*, vol. 11(4) (2006) pp. 041126-1-041126-10. (10 pgs.).
Hammer et al., "Tracking Scanning Laser Ophthalmoscope (TSLO)," *Proceedings of SPIE*, vol. 4951 (2003) pp. 208-217. (10 pgs.).
Hammer, et al. "Hybrid LSLO/SDOCT retinal imager," [online], *Presented at SPIE BiOS 2007: Biomedical Optics Symposium and Exhibition* [retrieved on Jul. 31, 2007]. Retrieved from the Internet <URL:http//www.psicorp.com/publications/PDF/sr-1287.pdf> (9 pgs.).
Hammer, et al., "Technological Advances Improve Retinal Diagnostics," *Biophotonics International*, vol. 10(9) (2003) p. 20. (3 pgs.).
Hausler et al., "'Coherence Radar' and 'Spectral Radar'—New Tools for Dermatological Diagnosis," *Journal of Biomedical Optics*, vol. 3(1) (1998) pp. 21-31. (11 pgs.).
Heacock et al., "Imaging of the Choroid With the Scanning Slit Laser Ophthalmoscope (SSLO)," *The Society for Photo-Optical Instrumentation Engineers (SPIE)*, vol. 3591 (1999) pp. 456-464. (9 pgs.).
Huang et al., "Optical Coherence Tomography," *Science*, vol. 254 (1991) pp. 1178-1181. (4 pgs.).
Iftimia, et al. "Hybrid Retinal Imager Using Line-Scanning Laser Ophthalmoscopy and Spectral Domain Optical Coherence Tomography," *Optics Express*, vol. 14(26) (2006) pp. 12909-12914. (6 pgs.).
Ishikawa et al., "Retinal Nerve Fiber Layer Assessment Using Optical Coherence Tomography With Active Optic Nerve Head Tracking," *Investigative Ophthalmology & Visual Science*, vol. 47(3) (2006) pp. 964-967. (4 pgs.).
Johnson et al., "Laser Eye Injuries Among US Military Personnel," *Proceedings of SPIE*, vol. 4953 (2003) pp. 51-60. (10 pgs).
Kobayashi et al., "Confocal Scanning Laser Ophthalmoscope With a Slit Aperture," *Measurement Science and Technology*, vol. 2 (1991) pp. 287-292. (6 pgs.).
Leitgeb et al., "Performance of Fourier Domain vs. Time Domain Optical Coherence Tomography," *Optics Express*, vol. 11(8) (2003) pp. 889-894. (6 pgs.).
Liang et al., "Supernormal Vision and High-Resolution Retinal Imaging Through Adaptive Optics," *Journal of the Optical Society of America A*, vol. 14(11) (1997) pp. 2884-2892. (9 pgs.).
Martin et al., "Direct and Noninvasive Assessment of Parafoveal Capillary Leukocyte Velocity," *American Academy of Ophthalmology*, vol. 112(12) (2005) pp. 2219-2224. (6 pgs.).
Nassif et al., "In Vivo High-Resolution Video-Rate Spectral-Domain Optical Coherence Tomography of the Human Retina and Optic Nerve," *Optics Express*, vol. 12(3) (2004) pp. 367-376. (10 pgs.).
Park et al., "Real-Time Multi-Functional Optical Coherence Tomography," *Optics Express*, vol. 11(7) (2003) pp. 782-793. (12 pgs.).
Patton et al., "Retinal Image Analysis: Concepts, Applications and Potential," *Progress in Retinal and Eye Research*, vol. 25 (2006) pp. 99-127. (29 pgs.).
Podoleanu et al., "Combinations of Techniques in Imaging the Retina with High Resolution," *Progress in Retinal and Eye Research*, vol. 27 (2008) pp. 464-499. (36 pgs.).
Podoleanu et al., "Combined Optical Coherence Tomograph and Scanning Laser Ophthalmoscope," *Electronics Letters*, vol. 34(11) (1998) (2 pgs.).
Podoleanu et al., "Combing SLO and OCT technology," *Bulletin De La Société Belg D'Opthalmologie 2006 LNKD*-PubMed: 17265795, No. 302 (2006) pp. 133-151. (19 pgs.).
Roach et al., "Retinal Response of *Macaca mulatta* to Picosecond Laser Pulses of Varying Energy and Spot Size," *Journal of Biomedical Optics*, vol. 9(6) (2004) pp. 1288-1296. (9 pgs.).
Roorda et al., "Adaptive Optics Scanning Laser Ophthalmoscopy," *Optics Express*, vol. 10(9) (2002) pp. 405-412. (8 pgs.).
Sakaguchi et al., "Amsler Grid Examination and Optical Coherence Tomography of a Macular Hole Caused by Accidental Nd: YAG Lasser Injury," *American Journal of Ophthalmology*, vol. 130(3) (2000) pp. 355-356 (2 pgs.).
Sasahara et al., "Optical Coherence Tomographic Observations Before and After Macular Hole Formation Secondary to Laser Injury," *American Journal of Ophthalmology*, vol. 136(6) (2003) pp. 1167-1170. (4 pgs.).
Thibos et al., "Standards for Reporting the Optical Aberrations of Eyes," *Journal of Refractive Surgery*, vol. 18 (2002) pp. S652-S660. (9 pgs.).
Vogel et al., "Retinal Motion Estimation in Adaptive Optics Scanning Laser Ophthalmoscopy," *Optics Express*, vol. 14(2) (2006) pp. 487-497. (11 pgs.).
Webb et al., "Confocal Scanning Laser Ophthalmoscope," *Applied Optics*, vol. 26(8) (1987) pp. 1492-1499. (8 pgs.).
White et al., "In Vivo Dynamic Human Retinal Blood Flow Imaging Using Ultra-High-Speed Spectral Domain Optical Doppler Tomography," *Optics Express*, vol. 11(25) (2003) pp. 3490-3497. (8 pgs.).
Wojtkowski et al., "In Vivo Human Retinal Imaging by Fourier Domain Optical Coherence Tomography," *Journal of Biomedical Optics*, vol. 7(3) (2002) pp. 457-463. (7 pgs.).
Wojtkowski et al., "Real-Time In Vivo Imaging by High-Speed Spectral Optical Coherence Tomography," *Optics Letters*, vol. 28(19) (2003) pp. 1745-1747. (3 pgs).
Yun et al., "High-Speed Optical Frequency-Domain Imaging," *Optics Express*, vol. 11(22) (2003) pp. 2953-2963. (9 pgs.).
Yun et al., "High-Speed Spectral-Domain Optical Coherence Tomography at 1.3 μm Wavelength," *Optics Express*, vol. 11(26) (2003) pp. 3598-3604. (7 pgs.).
Xue et al., "Photoreceptor Counting and Montaging of En-Face Retinal Images from an Adaptive Optics Fundus Camera," *Journal of Optical Society of America A*, vol. 24(5) (2007) pp. 1364-1372. (9 pgs.).
International Search Report for International Application No. PCT/US2011/022060, Date of Mailing Aug. 18, 2011 (6 pgs.).

\* cited by examiner

MULTI-FUNCTIONAL ADAPTIVE OPTICS RETINAL IMAGING

CROSS REFERENCE TO RELATED APPLICATION

This application claims the benefit of and priority to U.S. Provisional Patent Application No. 61/297,128 filed Jan. 21, 2010, which is owned by the assignee of the instant application and the disclosure of which is incorporated herein by reference in its entirety.

GOVERNMENT RIGHTS

The invention was made with government support under NIH National Eye Institute grant no. 1R43EY018986-01. The government may have certain rights in the invention.

FIELD OF THE INVENTION

The invention relates generally to retinal imaging, and more particularly, to a multi-functional retinal imaging system that combines adaptive optics corrected optical coherence tomography and scanning laser ophthalmoscopy channels.

BACKGROUND

Adaptive optics (AO) and optical coherence tomography (OCT) can provide information on cellular and sub-cellular structures in the live eye. OCT uses low-coherence interferometry to de-link axial resolution from the diffraction-limited depth-of-field for generation of micron-level axial resolution optical depth sections. AO is a technique to enhance the transverse resolution and depth sectioning capabilities by detection and correction of ocular aberrations. It has been integrated into instruments for full-field fundus imaging, scanning laser ophthalmoscopy (SLO), and Fourier domain (FD) OCT.

AO has also become a staple for vision researchers as a tool to explore the structural and functional aspects of vision and its disruption by disease. While AO has yet to make a full transition from research lab to clinic, OCT is now a standard diagnostic procedure for glaucoma, macular holes, macula edema, retinal detachments, and other retinal pathologies. FDOCT has now supplanted time domain (TD) OCT because of its advantages of higher speeds (near video rate), higher signal-to-noise ratio via simultaneous multiplexed acquisition of depth voxels, and lower phase noise. Clinical FDOCT systems are available commercially from several companies.

FDOCT comes in two basic varieties depending upon whether the source arm (swept source, SS) or the detection arm (spectral domain, SD) of the interferometer is altered. Each technique has advantages and disadvantages, but in general, SDOCT systems have slightly better axial resolution and SSOCT systems have increased depth range and accessibility to longer wavelengths. Ophthalmic OCT research systems at 1 μm, including initial reports configured with AO have shown significantly improved choroidal penetration compared to 850 nm systems. In addition to increased penetration, ocular dispersion is less at 1 μm than at 850 nm.

SLO and OCT are complementary tools for imaging the retina. OCT is an interferometric technique, whose fast 2-D frame axis is cross-sectional (i.e., lateral-axial) with micron level axial resolution that yields excellent sectioning capability. OCT is therefore better suited for visualization of retinal layers. SLO is a confocal technique whose fast 2-D frame axis is en-face (i.e. lateral-lateral) with sensitivity to multiply-scattered light. SLO is therefore better able to resolve photoreceptors, blood flow, and capillaries with higher contrast than OCT. Also, SLO systems can be configured to collect fluorescence signals.

SUMMARY OF THE INVENTION

The invention, in one embodiment, features a multi-functional retinal imager that combines adaptive optics-corrected Fourier domain optical coherence tomography and scanning laser ophthalmoscopy channels. The adaptive optics provide high lateral resolution and a narrow depth of focus by real-time correction of ocular aberrations that distort the wavefront and blur the focused beam in the eye. OCT is a technique for micron-level axial resolution and depth sectioning. The technology can include both spectrometer-based and swept source-based FDOCT implementations. A wide field line scanning ophthalmoscope (LSO) and a retinal tracker (RT) can also be included in the system. In certain embodiments, a retinal imaging system can combine AO-corrected scanning laser ophthalmoscopy, swept source Fourier domain optical coherence tomography imaging, and wide field line scanning ophthalmoscopy imaging modes, and retinal tracking in a single, compact clinical platform.

In one aspect, the technology features an optical apparatus including a system of optical components capable of operating in a scanning laser ophthalmoscope (SLO) mode and an optical coherence tomography (OCT) mode. The system of optical components includes a first optical module for the SLO mode, a second optical module for the OCT mode, and a first scanning device. The first optical module for the SLO mode includes a first source adapted to provide a first imaging beam for the SLO mode and a first detection device configured to receive a first signal associated with a first image of a retina of an eye. The second optical module for the OCT mode includes a second source adapted to provide a second imaging beam for the OCT mode and a second detection device configured to receive a second signal associated with a second image of the retina. The first scanning device is configured to move the first imaging beam along the retina in the slow axis of the SLO mode to acquire the first image and (ii) to move the second imaging beam along the retina in the fast axis of the OCT mode to acquire the second image.

In another aspect, there is a method of imaging a retina of an eye. The method includes acquiring a SLO image of the eye by receiving, on a first detector, a first light returning from the eye and providing a first electrical signal responsive to the first light at each of a plurality of locations along the first detector. The first electrical signal is indicative of the SLO image of the eye. The method includes acquiring an OCT image of the eye by receiving, on a second detector, a second light returning from the eye and providing a second electrical signal responsive to the second light at each of a plurality of locations along the second detector. The second electrical signal is combined with a reference signal from a reference arm. The second electrical signal and the reference signal are associated with the OCT image of the eye. The method also includes scanning, using a first scanning device, (i) a first imaging beam along the retina in the slow axis of the SLO mode to acquire the SLO image and (ii) a second imaging beam along the retina in the fast axis of the OCT mode to acquire the OCT image.

In yet another aspect, there is an optical apparatus including a system of optical components capable of operating in a scanning laser ophthalmoscope (SLO) mode and an optical coherence tomography (OCT) mode. The system of optical components includes at least two spherical mirrors, at least two deformable mirrors (DM's) positioned behind the at least two spherical mirrors, a beamsplitter positioned behind the at least two deformable mirrors, an OCT optical module introduced by the beamsplitter, and a SLO optical module behind the beamsplitter. Each spherical mirror has a diameter greater than 20 cm and is positioned relative to the eye. The optical apparatus also includes first, second and third scanning devices. The first scanning device is positioned between the beamsplitter and the eye. The first scanning device is configured (i) to move a first imaging beam along the retina in the slow axis of the SLO mode to acquire an SLO image and (ii) to move a second imaging beam along the retina in the fast axis of the OCT mode to acquire an OCT image. The second scanning device is positioned behind the beamsplitter. The second scanning device is configured to move the first imaging beam along the retina in the fast axis of the SLO mode to acquire the SLO image. The third scanning device is positioned between the beamsplitter and the eye. The third scanning device is configured to move the second imaging beam along the retina in the slow axis of the OCT mode to acquire the OCT image.

In other examples, any of the aspects above, or any apparatus, system or device, or method, process or technique, described herein, can include one or more of the following features. In various embodiments, the OCT mode can include a Fourier domain OCT channel configured to be spectrometer-based or swept source-based. The system of optical components can be adapted to simultaneously image the same retinal coordinates in the SLO mode and OCT module.

In certain embodiments, the optical apparatus includes a second scanning device configured to move the first imaging beam along the retina in the fast axis of the SLO mode to acquire the first image and a third scanning device configured to move the second imaging beam along the retina in the slow axis of the OCT mode to acquire the second image. The first scanning device, the second scanning device and the third scanning device can be positioned at pupil conjugates in the system of optical components. The first scanning device can be mounted to the third scanning device at a pupil conjugate.

In various embodiments, the second imaging beam of the OCT mode is introduced by a beamsplitter positioned between the eye and the SLO module. The third scanning device can be configured to scan the first imaging beam to generate a mosaic image of the eye.

In some embodiments, a third optical module is configured to (i) detect an optical distortion and (ii) correct the optical distortion in at least one of the first or second imaging beams scanned on the eye. The third optical module can include a wavefront sensor adapted to detect the optical distortion and a wavefront compensator adapted to correct the optical distortion in the first or second imaging beam. In certain embodiments, two wavefront compensators are positioned between the beamsplitter and the eye. A dual-deformable mirror configuration can be used to provide simultaneous, high-fidelity, wide dynamic range correction of lower- and higher-order ocular aberrations.

A fourth optical module can be configured to operate in a line scanning ophthalmoscope (LSO) mode. The fourth optical module can include a third source adapted to provide a third imaging beam in a line focus configuration for the LSO mode. The fourth optical module can be configured to (i) scan the third imaging beam in the line focus configuration along the retina in a second dimension and (ii) descan the second light returning from the eye in the second dimension. The light returning from the eye is directed to a third detection device.

The system of optical components can include a fifth optical module adapted to track a reference feature of the retina of the eye. The first optical module can be adapted to control the position of the first imaging beam relative to the reference feature to correct for motion of the eye. The system of optical components can include a sixth optical module adapted to provide a fluorescence imaging channel. A LCD-based fixation target can be used to acquire images of the eye in at least one of the SLO mode, the OCT mode, or the LSO mode.

In various embodiments, the system of optical components includes at least two spherical mirrors. Each spherical mirror has a diameter greater than 20 cm. The spherical mirrors are positioned relative to the eye and configured to provide a field of view greater than 30 degrees. The wavelength of the second imaging beam of the OCT mode can be selected to match a physical property of the tissue.

The optical system can be used for one or more of the following applications:
  Retinal layer quantification and mapping
  Photoreceptor quantification and mapping
  Retinal vasculature mapping
  Retinal flow (FDOCT channel in Doppler mode)
  Diagnosis and early detection of retinal diseases such as diabetic retinopathy (DR), age-related macular degeneration (AMD), retinitis pigmentosa (RP), and retinopathy of prematurity (ROP).
  Drug development and determination of efficacy
  Vision studies
  Small animal imaging Other aspects and advantages of the invention will become apparent from the following detailed description, taken in conjunction with the accompanying drawings, illustrating the principles of the invention by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DESCRIPTION OF THE INVENTION

Figure 1:
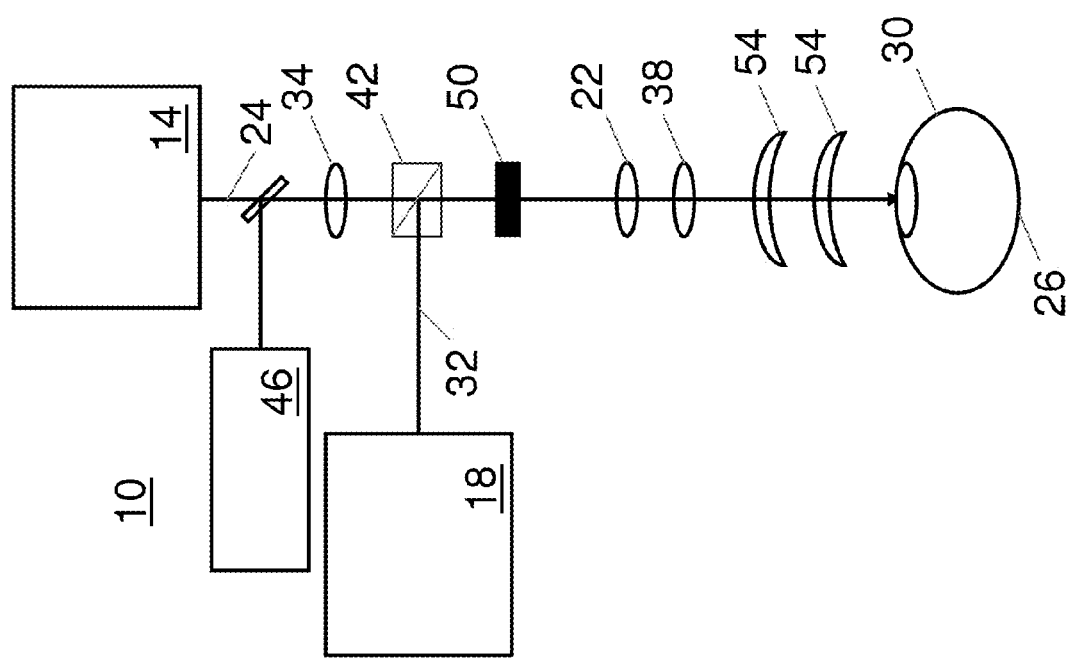
FIG. 1 shows a schematic diagram of an optical apparatus for imaging a retina of an eye.

FIG. 1 shows an optical apparatus 10 including a system of optical components capable of operating in a scanning laser ophthalmoscope (SLO) mode and an optical coherence tomography (OCT) mode. The system of optical components includes a first optical module 14 for the SLO mode, a second optical module 18 for the OCT mode, and a first scanning device 22. The first optical module 14 for the SLO mode includes a first source adapted to provide a first imaging beam 24 for the SLO mode and a first detection device configured to receive a first signal associated with a first image of a retina 26 of an eye 30. The second optical module 18 for the OCT mode includes a second source adapted to provide a second imaging beam 32 for the OCT mode and a second detection device configured to receive a second signal associated with a second image of the retina 26. The first scanning device 22 is configured to move the first imaging beam along the retina 26 in the slow axis of the SLO mode to acquire the first image and to move the second imaging beam along the retina 26 in the fast axis of the OCT mode to acquire the second image.

The optical apparatus 10 can include a second scanning device 34 and a third scanning device 38. The second scanning device 34 can be configured to move the first imaging beam along the retina in the fast axis of the SLO mode to acquire the first image. The third scanning device 38 can be configured to move the second imaging beam along the retina in the slow axis of the OCT mode to acquire the second image. The first scanning device 22, the second scanning device 34 and the third scanning device 38 can be positioned at pupil conjugates in the system of optical components. In certain embodiments, the first scanning device 22 is mounted to the third scanning device 38 at a pupil conjugate. The third scanning device 38 can be configured to scan the first imaging beam to generate a mosaic image of the eye.

A beamsplitter 42 can be used to introduce the second imaging beam of the OCT mode. The beamsplitter 42 can be positioned between the eye 30 and the SLO module 14. The optical apparatus 10 can include a third optical module configured to (i) detect an optical distortion and (ii) correct the optical distortion in at least one of the first or second imaging beams scanned on the eye. The third optical module can include a wavefront sensor 46 adapted to detect the optical distortion and at least one wavefront compensator 50 adapted to correct the optical distortion in the first or second imaging beam. In certain embodiments, a first wavefront compensator and a second wavefront compensator are positioned between the beamsplitter 42 and the eye 30.

The optical apparatus 10 can include at least two spherical mirrors 54. Each spherical mirror 54 can have a large surface area. For example, each spherical mirror 54 can have a diameter greater than 20 cm. The spherical mirrors 54 can be positioned relative to the eye and configured to provide a field of view greater than 30 degrees. In some embodiments, the field of view is about 15 to 35 degrees. An advantage of the wide field front end is that the SLO and OCT scans can be made large. A user can perform an initial low resolution, large scan to map the entire macula and then perform a high resolution scan of specific targets.

Figure 2:
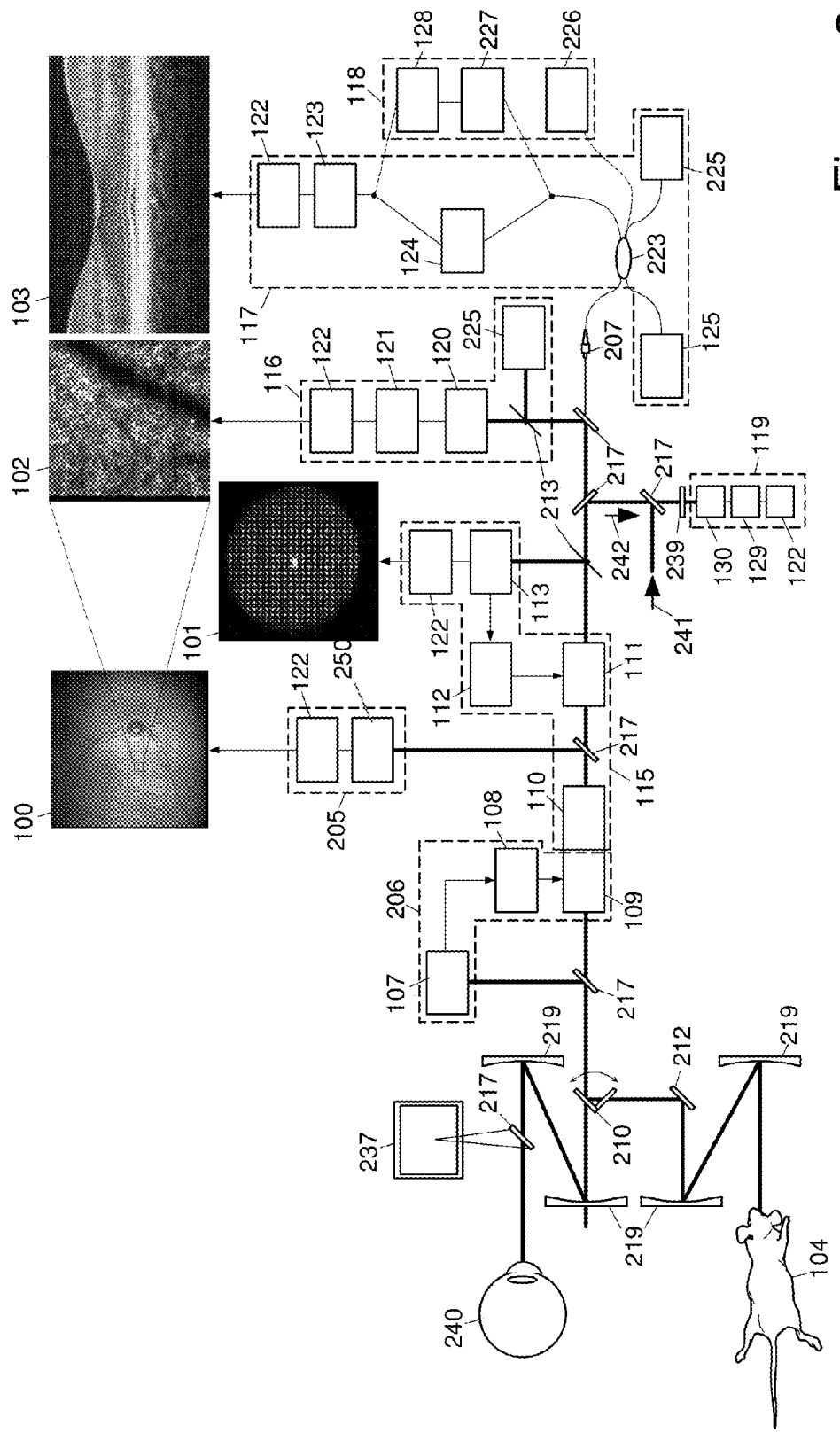
FIG. 2 shows a block diagram of an exemplary multimodal AO system.

FIG. 2 shows a block diagram of an exemplary multimodal AO system. The optical design can significantly reduce inherent aberrations providing a wide field of regard (for example, ~33 degrees) for the SLO and SSOCT fields while fully integrating the LSO imaging and RT reflectometer. The AO components can include a Hartmann-Shack wavefront sensor (HS-WS) and two deformable mirrors in a woofer-tweeter configuration for high-fidelity, wide dynamic range correction of lower- and higher-order ocular aberrations. Other features of the system include a custom, FPGA-based OCT digitizer and processing board and a high resolution LCD-based fixation target. The design achieves an extremely compact instrument footprint suitable for clinical portability. The system performance was validated on model eyes and human and animal subjects.

FIG. 2 shows a LSO image 100, a HS-WS image 101, an AOSLO image 102 and FDOCT image 103. The imaging system shown in FIG. 2 can be used to image human eyes 240 or animals 104. The imaging system includes a first module/SLO channel 116, a second module/FDOCT channel (e.g., a spectrometer-based FDOCT channel 117 or a swept source based FDOCT channel 118), a third module/AO module 115, a fourth module/LSO channel 205, a fifth module/retinal tracker 206, and a sixth module/fluorescence channel 119.

The SLO channel 116 includes a source 225 (e.g., a superluminescent diode), a detection device 120 (e.g., a confocal detector), a SLO timing board 121, and a framegrabber 122. The FDOCT channel can be a spectrometer-based FDOCT channel 117 or a swept source based FDOCT channel 118 coupled to the optical system by a fiber connector 207. Both FDOCT channels includes a framegrabber 122, a real-time FDOCT processor/controller 123, an optical delay line 125, and a fiber coupler 223. The SDOCT 117 utilizes a source 225 (e.g., a superluminescent diode) and a spectrometer 124. The SSOCT 118 utilizes a swept source 226, a high speed digitizer 128 and a balanced detector 227.

The third module/AO module 115 includes image scanners 110, at least one deformable mirror/wavefront compensator 111, a DM controller 112, a HS-WS 113, and a framegrabber 122.

The fourth module/LSO channel 205 includes a LSO module 250 and a framegrabber 122. The fifth module/retinal tracker 206 includes a tracker source and reflectometer 107, a tracker controller 108, and tracker scanners 109. An exemplary LSO system is described in U.S. Pat. No. 6,758,564, the disclosure of which is herein incorporated by reference in its entirety. The LSO can be combined with a retinal tracking system to form a TSLO. An exemplary tracking system is described in U.S. Pat. No. 5,797,941, the disclosure of which is herein incorporated by reference in its entirety. Stabilized retinal imaging with adaptive optics is described in U.S. Pat. No. 7,758,189, the disclosure of which is herein incorporated by reference in its entirety. A hybrid LSLO/OCT instrument is described in U.S. Pat. No. 7,648,242, the disclosure of which is herein incorporated by reference in its entirety. An adaptive optics line scanning ophthalmoscope is described in U.S. Patent Publication No. 2010/0195048, the disclosure of which is herein incorporated by reference in its entirety.

The sixth module/fluorescence channel 119 includes a fluorescence excitation beam 241, a fluorescence emission beam 242, a wavelength selection filter 239, a pre-amplifier 129, a photomultiplier tube (PMT) 130, and a framegrabber 122. The source can be any fluorescent source (e.g., white light, laser, SLD, LED, etc.) with sufficient power to excite the appropriate retinal fluorophores. The fluorescence channel can include dichroic beamsplitters to combine visible excitation and emission beam with NIR imaging beams and to separate excitation and emission beams. The filter 239 can be a barrier (notch) filter to remove all wavelengths except fluorescence on the PMT detector. A filter can be selected based on the desired fluorophore.

The imaging system shown in FIG. 2 includes various beamsplitters and optics for coupling the various modules so that measurements can be taken. Beamsplitters include pellicle beamsplitter 213 and dichroic beamsplitters 217. One skilled in the art will recognize that other optics can be used to couple the optical modules. Spherical mirrors 219 can be used to provide a wide field of view. The imaging system can include a LCD-based fixation target 237.

The imaging system can be configured to accommodate two or more output pupil sizes. For example, an optical component 210 can be used to couple a second optical imaging line to the instrument. In certain embodiments, the optical component is a flip mount. In some embodiments, this is desirable so that animals 104 can be imaged or so that humans with different pupil sizes can be imaged. An integrated small animal imaging port (accessed from a flip mounted mirror) can change the pupil magnification for AO-correction in small animals, which have smaller dilated pupil sizes. The beam diameter at the output for two exemplary configurations is 7.5 and 2.5 mm. Smaller pupil sizes can provide for larger depth of focus. The optical component or the flip mount can be actuated manually or automatically by a motor controlled by software on a computer.

A wide field (>30 degree) optical design allows high resolution image field (typically 1-3 degrees) to be placed anywhere in the larger field of regard without re-positioning the patient or moving the fixation target. In certain embodiments, the field is about 15 to 35 degrees. With dynamic AO correction, variability in system aberrations across the wide field of regard can be compensated in real-time. Placing optical elements at pupil conjugates and introducing beams with dichroic beamsplitters allows simultaneous acquisition of AO-correct SLO and OCT images. The SLO resonant scanner is placed behind the DMs and the OCT beam is introduced with a dichroic beamsplitter between the resonant scanner and the DMs. The HS-WS is acquired synchronously so that AO-correction is uniform across the SLO or OCT image field. The instrumentation is also can be designed so that the LSO image is acquired and the RT operates simultaneously. The SLO and OCT images can be registered (e.g., imaging same retinal coordinates).

A dual-DM configuration can provide simultaneous high-fidelity, wide dynamic range correction of lower- and higher-order ocular aberrations. This allows AO corrections to be applied to a broader clinical population. The lower-order aberrations (up to 5 Zernike orders) are corrected with a very high-stroke DM with a lower number of actuators. The higher order aberrations (up to 8 Zernike orders) are corrected with a high-actuator count DM with a lower stroke.

The optical system includes an integrated LSO/RT optical head and beam path. The optics and instrumentation are slightly less complex with the fully integrated LSO/RT beam paths. This is made possible by the wide field optical design. The LSO and RT beams are typically at different wavelengths than the SLO and OCT beams.

Figure 3:
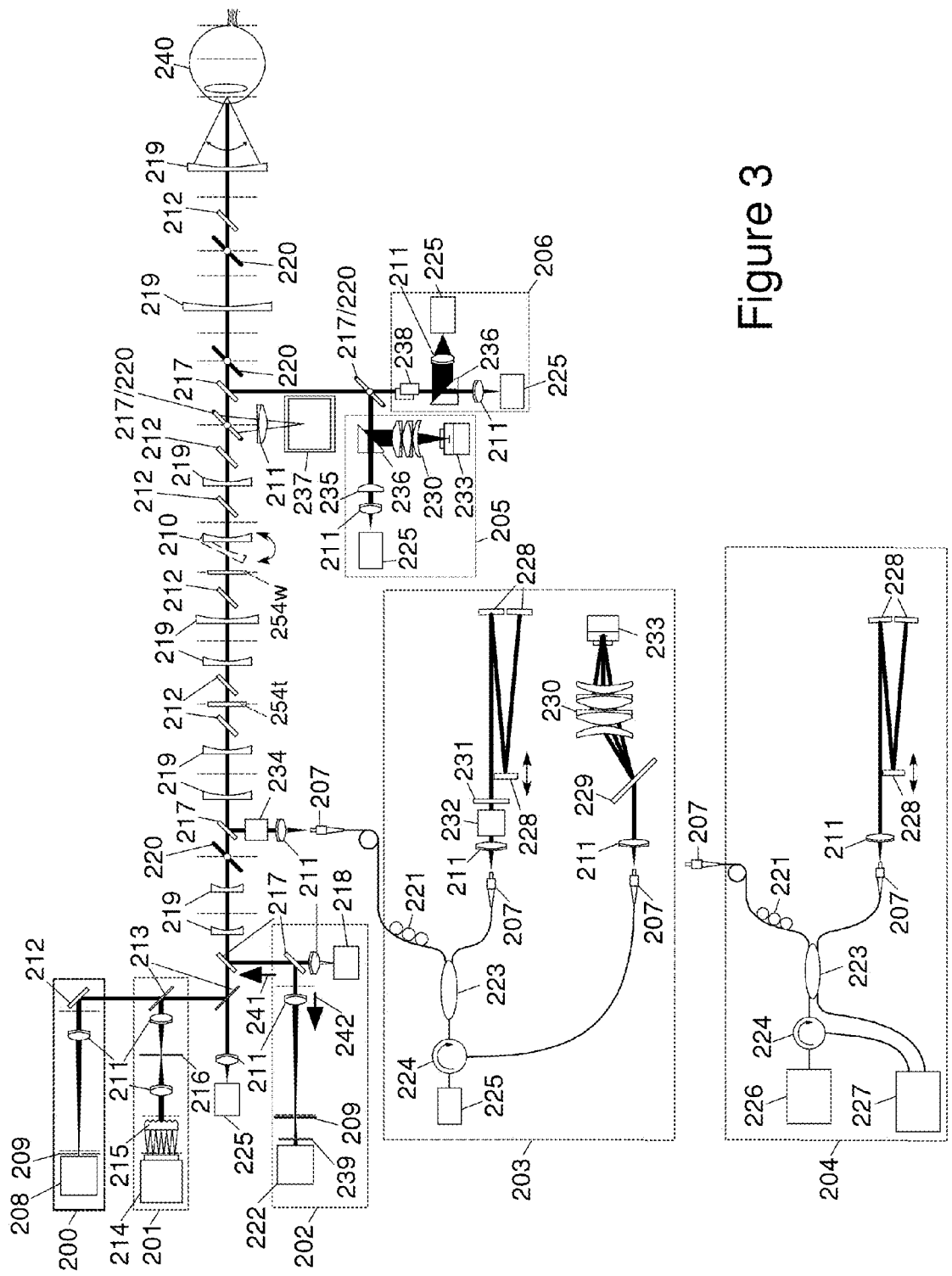
FIG. 3 shows an unfolded optical layout for a multimodal AO system.

FIG. 3 shows an unfolded optical layout. All imaging modes access a common beam path comprised of all-reflective optical elements to minimize chromatic aberrations and maintain high throughput. Ten spherical mirrors 219 are used to transfer and magnify (or minify) the retinal and pupil planes to successive conjugates. The magnification of each relay is set to nearly fill the physical dimensions of each component. All scanners and DMs are placed at pupil conjugates to pivot about and correct at a single plane. The tracking galvanometers are placed at conjugates to the eye's center-of-rotation to simultaneously track retinal and pupil shifts.

The SLO channel 200 utilizes a confocal pinhole 209 and an avalanche photodiode (APD) 208 to collect light returning from the retina and source 225.

The OCT channel can be configured in a spectrometer based 203 or a swept source-based 204 architecture. Both architectures can be fiber connected 207 to the main optical line by a dichroic beamsplitter 217, a lens 211 and an achromatizer 234. The spectrometer based OCT 203 utilizes a source 225, a circulator 224 fiber connected 207 to a detection device including a lens 211, a transmission grating 229, a series of objective lenses 230, and a linear detector 233. The SDOCT 203 also includes a polarization controller 221 and a 2×2 fiber coupler 223 fiber connected 207 to an optical delay line including a lens 211, dispersion compensation cube 232, a neutral density filter 231 and mirrors 228. The optical delay line uses a folded arrangement—five passes off the mirrors 228—to match the ~4.3 m sample pathlength.

The swept source-based OCT 204 utilizes a swept source 226, a circulator 224 connected to a balanced detector 227 and a fiber coupler 223. The SSOCT 204 includes a polarization controller 221 and an optical delay line. The balanced detector provides efficient light collection and common mode signal rejection.

The AO design includes a dual mirror 254 (e.g., woofer 254*w* and tweeter 254*t*) AO approach for optimal aberration compensation. The Hartmann-Shack wavefront sensor (HS-WS) 201 uses a lenslet array 215 and CCD camera 214 to sample the wavefront across the pupil. A lens relay 211 and iris 216 are used in front of the HS-WS 201 to reduce reflection artifact from the cornea. The predominant system aberrations are defocus and astigmatism, which can be corrected with either the woofer 254*w* or the tweeter 254*t*, but better corrected with the woofer because it constitutes a smaller fraction of its total range. The system RMS error can be 0.64λ (0.48 µm). The Mirao requires a total surface stroke of ~1.5 µm to correct system aberrations. The maximum stroke needed over the entire 33-deg. field for system aberration is <4 µm.

The LSO module 205 includes a source 225, a lens 211 and a cylindrical lens 235 to form a line of light. An aperture splitter 236 can pick off light returning from the eye so it can be directed to a linear detector through a series of objective lens 230. A scanner 217/220 scans the imaging beam in the line focus configuration along the retina in a second dimension and descans the second light returning from the eye in the second dimension. The LSO provides a wide field (~33 deg.) confocal view of the retina for scan placement and initial target identification.

The retinal tracker (RT) hardware can be fully integrated into the AO beam path to provide optimal tracking performance. The active retinal tracker operates by directing and dithering (at 16 kHz) a beam onto a retinal target (usually the bright lamina cribrosa in the optic nerve head) and sensing with a confocal reflectometer phase shifts when the eye moves the target off the dither circle. The resultant error signals are fed back in high speed closed loop fashion into two transverse galvanometers to maintain lock. In addition to having an integrated design for AO applications, the retinal tracker configuration includes an FPGA-based tracking control board, which performs digital lock-in amplification and other signal processing for robust operation. The tracking system maintains lock with a bandwidth greater than 1 kHz (limited only by the galvanometer inertial constraints) and an accuracy <15 μm.

The RT module 206 includes a dual source 225, focusing lens 211, an aperture splitter 236, and a resonant scanner 238.

The fluorescence channel 202 channel includes source 218 and a lens 211 for delivering fluorescence excitation beam 241 and lens 211, pinhole 209, filter 239 and PMT 222 for collecting fluorescence emission beam 242.

The 1-μm swept source for OCT imaging can have an average output power of 11 mW, a bandwidth (BW) of 79 nm centered at ~1070 nm, and a duty cycle of 0.65. This bandwidth has a theoretical axial resolution of 4.6 μm in tissue. The wavelength of the OCT illumination beam can be selected to match a physical property of the tissue being imaged. The wavelength can be from 400 nm to about 2.6 microns, although longer or shorter wavelengths can be used depending on the chromophore. Exemplary features to target include the retina or a portion of the retina, blood, retinal pigment epithelial (RPE) cells, a feeder vessel, a drusen, a small tumor, a microaneurysm, or an epiretinal membrane. For example, a wavelength of 680 nm can be used to monitor blood flow in the retina.

An OCT illumination wavelength of 1 micron has certain advantages over 850 nm illumination, including in penetration depth into the retina. Choroid and sclera can be imaged. 1 micron scatters less than 850 nm in the eye. Other wavelengths can be used to target or match the optical or light tissue interaction properties of specific layers, cells, organelles or molecules in the retina.

All other illumination sources are superluminescent diodes (SLD) that reduce image speckle and tracker noise. The SLO illumination beam centered at ~750 nm (14 nm BW) also acts as the wavefront sensor beacon. The LSO illumination beam is centered at 830 nm (26 nm BW) and the tracker beam is centered at ~915 nm. All sources are combined with off-the-shelf dichroic beamsplitters except for D2, which can be custom made to transmit both the 1-μm OCT and 750-nm SLO NIR beams while reflecting the 830-nm LSO and 915-nm RT beams. Despite the number of beams, the instrument is still eye-safe because NIR wavelengths are used: the combined power is low, several times below ANSI thresholds even when all scanners fail.

The OCT/SLO scan engine is configured to use a resonant scanner (RS) and single galvanometer for SLO imaging and two galvanometers for OCT imaging. The OCT scan (line, circle, raster, radial, etc.) can be translated and centered anywhere in the wide field of the AO beam path by adjusting offset voltages to the galvanometers. Similarly, the SLO flying spot raster scan can be centered and shifted anywhere in the AO beam path for acquisition of montages and strips. However, because the SLO RS cannot be driven with voltage offsets, the x-axis OCT galvanometer serves the dual function of shifting the SLO raster in this mode.

The imaging system shown in FIG. 3 includes various beamsplitters, lens, mirrors and optics for coupling the various modules so that measurements can be taken. Beamsplitters include pellicle beamsplitter 213 and dichroic beamsplitters 217. One skilled in the art will recognize that other optics can be used to couple the optical modules. Turning mirrors 212 can be used to fold the optical design. Spherical mirrors 219 can be used to provide a wide field of view. The imaging system can include a LCD-based fixation target 237. The imaging system can include an optical component (such as a flip mount) 210 for an animal port.

Figure 4:
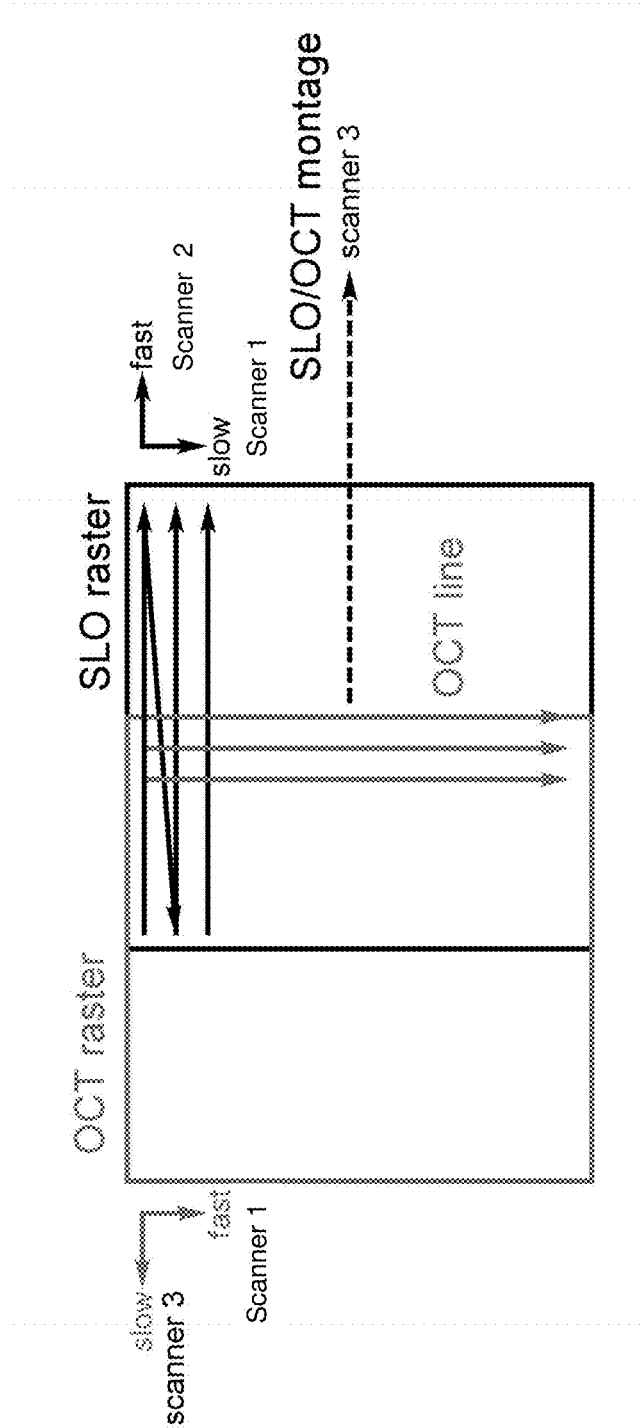
FIG. 4 shows a schematic diagram of scanning axes for the SLO and OCT.

FIG. 4 shows a schematic diagram of scanning axes for the SLO and OCT. The SLO flying spot raster is created from the fast axis of scanner 1 and the slow axis of scanner 2. The OCT line or rater is created from the fast axis of scanner 2 and the slow axis of scanner 3. Each scanner can be a galvanometer or other scanning optic known in the art. Scanner 3 can be used to create OCT raters or SLO montages or mosaics (e.g., stitching several high-resolution, low field images together to create a single high-resolution high-field image.

Figure 5:
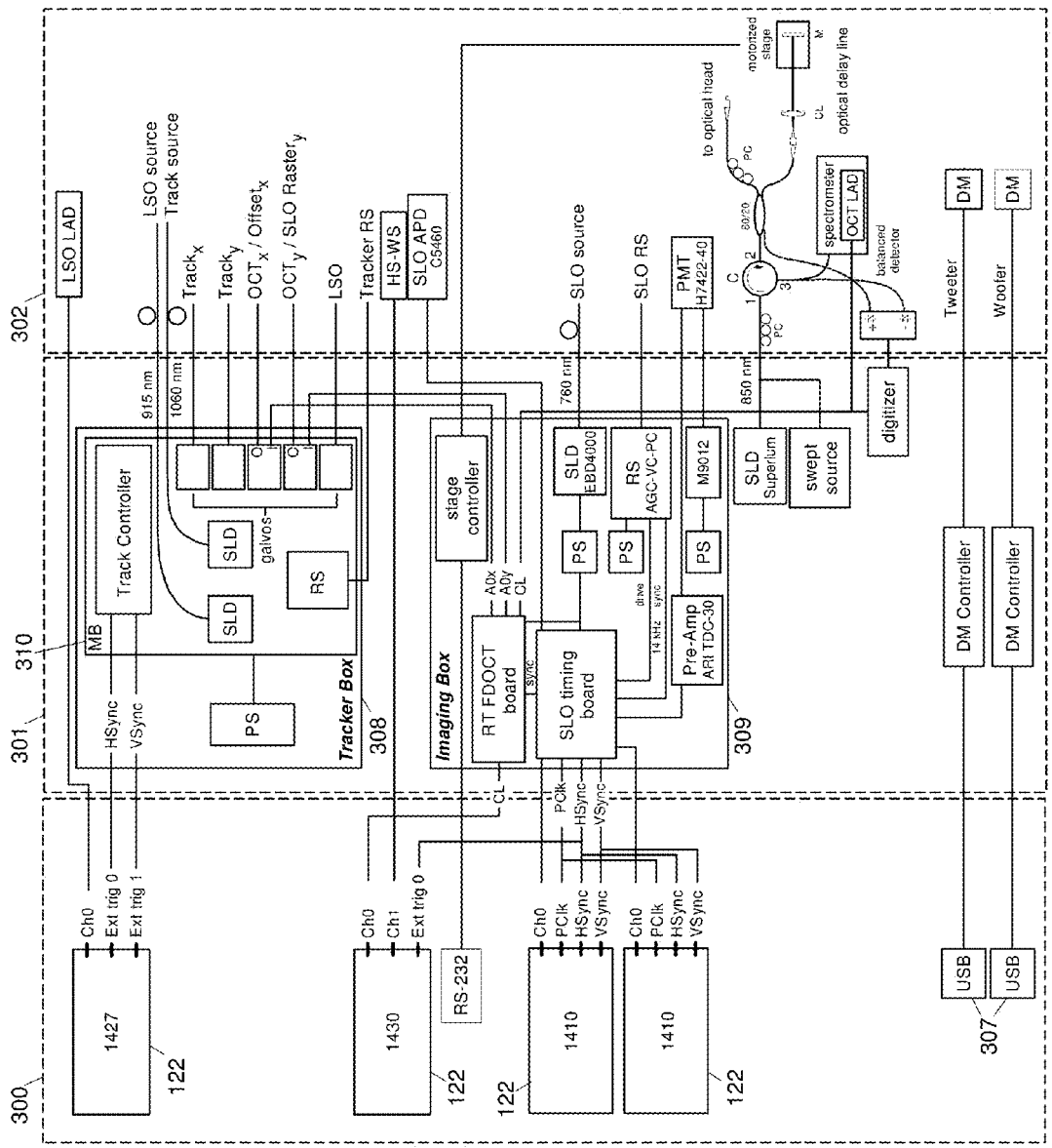
FIG. 5 show an example of an instrumentation layout.

FIG. 5 show an example of an instrumentation layout. In FIG. 5, box 300 represents the host computer, box 301 represents the instrumentation rack, and box 302 represents the optical table. The host computer 300 includes framegrabbers 122 for acquiring images and USB ports 307 for the DM controllers. All system instrumentation can be contained in two electronics boxes—a tracker box 308 and an imaging box 309. The tracker box 308 contains the LSO/RT sources, the tracking RS pair, all the system galvanometers, and two custom electronic boards designed to control the retinal tracker in a high bandwidth closed loop manner. The custom track controller board is an FPGA-based real-time processor that controls all hardware, generates all timing and waveform signals and performs the high-speed closed-loop feedback control. The custom tracking motherboard (MB) 310 can be designed so that all off-the-shelf OEM electronic driver boards can be plugged into the system with minimal wiring. The RT control board, OEM resonant scanner and galvanometer boards plug into the MB, which can include an integrated detector and driver/thermo-electric coolers for 2 SLDs.

The imaging box 309 contains the real time OCT digitizer and processing board, the SLO source and voltage-controlled RS driver board, and OCT depth stage controller. The RS amplitude (which sets the SLO size) is controlled via the host computer with an analog waveform output from a USB DAQ. The OCT image processing chain can be processed using a graphical processor unit (GPU) on a standard video card.

To provide seamless switching between OCT and SLO modes using the same scanning and processing hardware, a switch directs either the RS or swept source sync signals to the high speed digitizer. Both are TTL signals in the kHz range. The digitizer generates a pixel clock (50 MHz), duplicates the line sync, and generates a frame sync signal, which is passed to the framegrabbers via the real time OCT processing board. The real time processing board generates all the waveforms to drive the galvanometers. Thus the HS-WS camera (and hence the correction) is always synchronized to the primary imaging hardware. This prevents a drift in the AO correction across the imaging field. It is not necessary to synchronize the LSO scan. In OCT mode, the signal from the balanced detector generated from the fiber interferometer is input to the high speed digitizer. This signal is not used in SLO mode. Communication between the digitizer, real time OCT processing board, and framegrabbers is accomplished with the CameraLink interface. The hardware used to control the multimodal AO system also includes three framegrabbers (one dual camera), two cameras, two detectors, four sources, five galvanometers, 3 resonant scanners, a motorized stage, and two deformable mirrors.

The custom SLO timing board includes functionality for non-linear pixel clock generation for real-time image dewarping from the sinusoidal resonant scanner drive signal; electronic blanking (clamping) with a high-speed multiplexor for real-time analog signal conditioning; x-y galvanometer waveform generation; resonant scanner amplitude signal generation; dual channel operation for simultaneous reflectance/fluorescence analog signal conditioning; and synchronization with the real-time SDOCT processing board.

The multimodal AO retinal imager was tested in six subjects to demonstrate performance capabilities. The subjects were aged between 23 and 53 years and the refractive error was between 0 and 7D (all myopes). A human subject protocol was approved by New England IRB prior to all imaging. All subjects gave informed consent to be imaged. Some of the subjects with small pupils were dilated to enhance AO correction. Subjects that were not dilated often had larger variability in AO and imaging performance, especially when imaging the fovea, which caused the pupil to constrict. All subjects used a bite bar for head stabilization and pupil centration.

The imaging sessions did not follow a set protocol but included OCT cross-sectional and raster scans (1-3 mm), SLO images (1- and 2-deg. fields), strip scans, and montages. The montage scans step the SLO offset galvanometers over a matrix with overlap, the size of which (2×2, 3×3, 4×4, etc.) is configured by the user. The SLO strip scanning is an innovation whereby the SLO offset galvanometers are slowly scanned in the horizontal or vertical direction to pan across a retinal patch and produce a stack of images that are significantly overlapping. This aids in automated registration, especially in the presence of excessive eye motion.

The system optical performance was characterized first using diffusely reflecting targets at various retinal (i.e., focal) conjugates. Next, the system and AO performance were tested using a model eye consisting of a 25-mm focal length (fl) achromat and a diffusely reflecting "retina." Finally, the AO correction performance was measured in live human eyes.

In initial human subject testing of the dual-DM approach, a control algorithm was used whereby the woofer corrected system, large amplitude and/or low-order sample aberrations and the tweeter corrected small amplitude and/or high-order sample aberrations. To prevent the dual-DM control from causing the correction to oscillate (especially since the response time differed between mirrors), the woofer was initiated first and run in static mode where it could correct the wavefront for a fixed number of cycles and then held while the tweeter was activated after the woofer was frozen and left in dynamic mode. Of course the number of static cycles chosen is critical to insure proper lower-order aberration correction. At the retinal conjugates and in the model eye, both DMs were used although the tweeter corrected only a very small amount of residual aberration.

The validation at retinal conjugates and in the model eye was performed by direct measurement of the point spread function (PSF) independent of the HS-WS at a plane conjugate to the SLO detector pinhole using a standard USB CCD camera. The magnification from the SLO confocal pinhole (and CCD position) to the retina is ~9.25 so a 100-μm pinhole projects to roughly 11 μm on the retina, or ~2.2 times the 4.9-μm Airy disc at 750 nm. A 200-μm pinhole (~22 μm on the retina) is less confocal allowing more scattered and aberrated light without improving imaging, while a 50-μm pinhole (5.4 μm on the retina) is tightly confocal: only 1.1 times the Airy disc. In general, images are first taken with the 100-μm pinhole, and the 50-μm pinhole is used for increased contrast in subjects with bright macula and the 200-μm pinhole is used for undilated subjects and subjects with dim macula.

Figure 6:
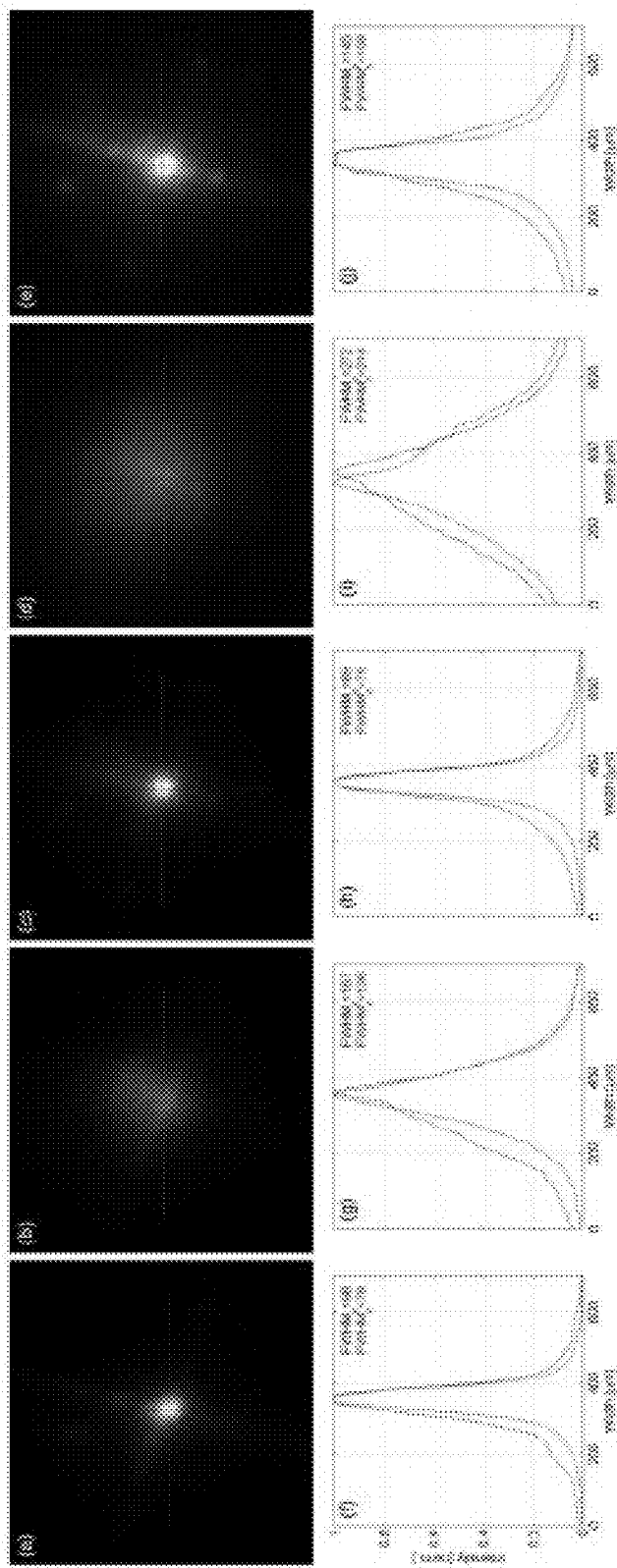
FIG. 6 shows the point spread functions (PSF's) at retinal conjugates two and four for focused illumination.

The PSFs at retinal conjugates two and four (see FIG. 3) for focused illumination are shown in the first three columns in FIG. 6. Note that the system aberration is minimal at r2, with some residual astigmatism. The PSF FWHM (full width half maximum, average of x and y) is 88 μm (9.5 μm at retina). At r4, however, there are significantly more lower order aberrations—the PSF FWHM nearly doubles to ~152 μm without AO correction. With AO correction, the PSF FWHM is 83 μm, less than two times the Airy disc size.

FIG. 6 also shows the PSFs in a model eye with and without AO correction (columns 4-5). With AO correction (both DMs activated), the FWHM decreases to ~127 from 243 μm. (The CCD may have been slightly saturated, causing a slight overestimation of the PSF width). Some residual astigmatism remains, but AO significantly improves the PSF approximately to the size of the confocal pinhole. In the model eye, AO correction reduced the RMS error from ~0.6 μm to <0.05 μm and increased the Strehl ratio to 0.92 (as measured by the wave aberration function from the HS-WS).

Figure 7:
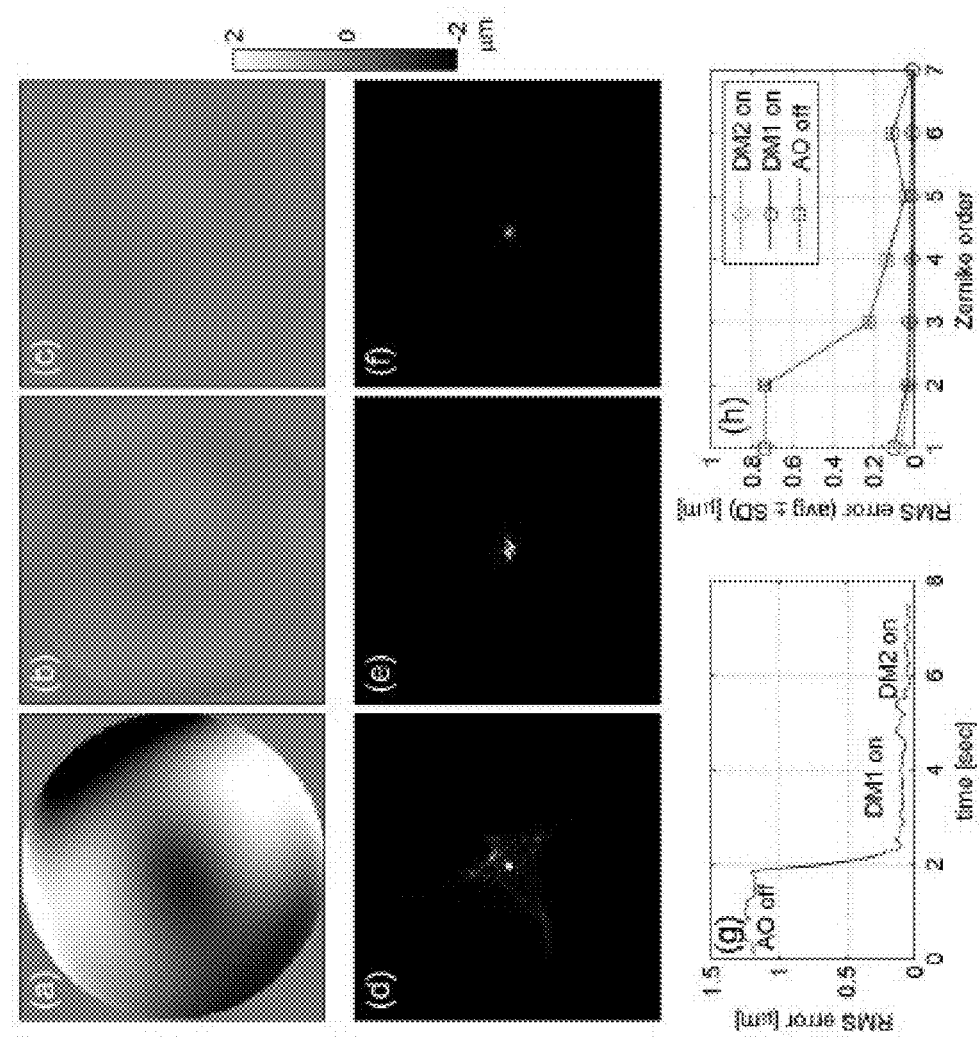
FIG. 7 shows an example of the AO performance achieved in one human subject.

An example of the AO performance achieved in one human subject is shown in FIG. 7. Shown are the wavefront error map (top row) and the PSF (second row) for three cases: no AO correction (first column), DM1 (woofer) correction (second column), and dual-DM (woofer-tweeter) correction (third column). The time course of the correction and the aberrations separated by Zernike order are also shown. The average RMS wavefront error (Strehl ratio) for the three cases was 1.215 (<0.01), 0.097 (0.52), and 0.052 (0.83) μm, respectively. Thus, the dual-DM approach achieved more optimal AO correction in human subjects than could be achieved with a single mirror alone.

Figure 8:
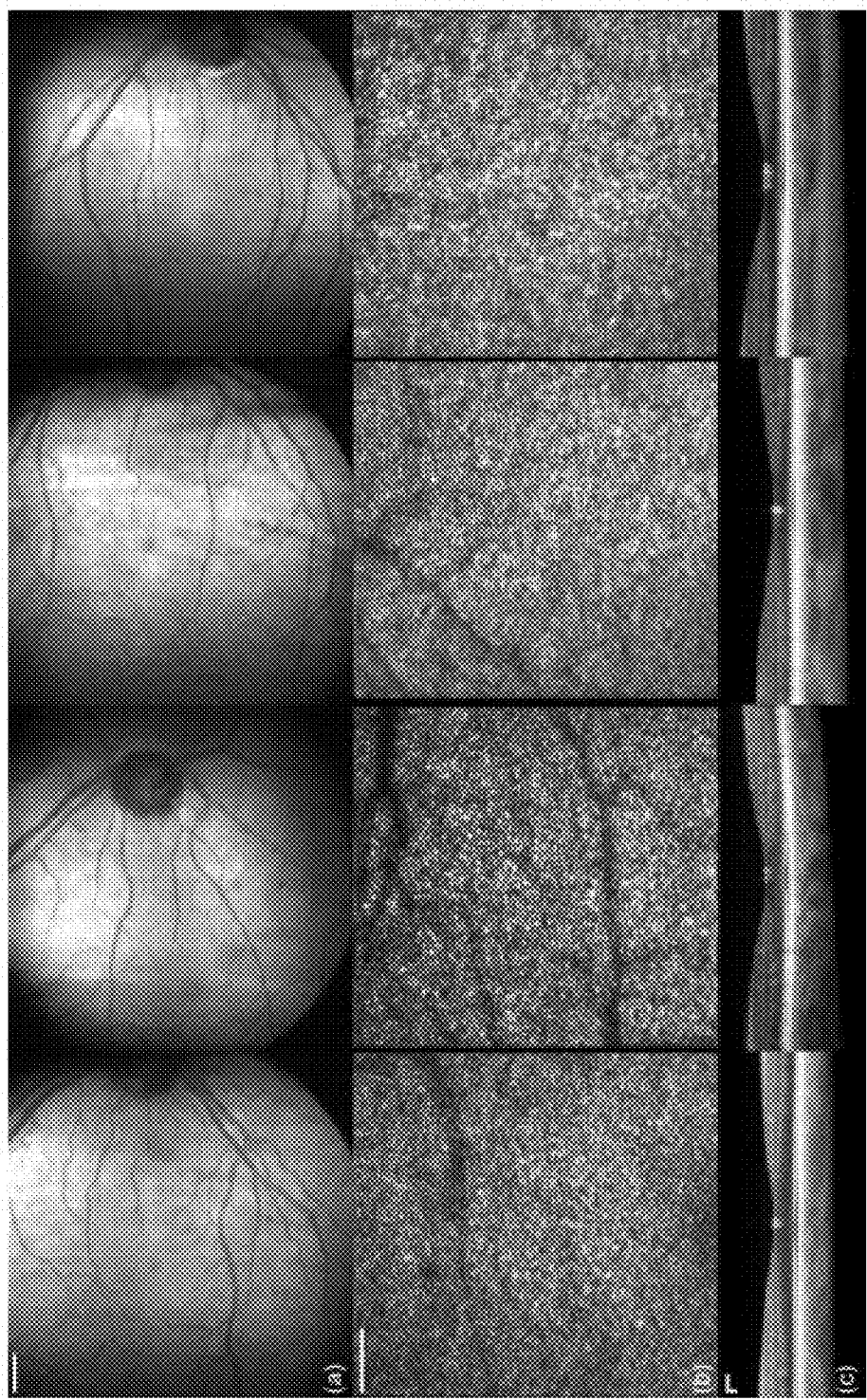
FIG. 8 shows examples from 4 of the 6 subjects in each of the three primary imaging modes (LSO, SLO, OCT).

Examples from 4 of the 6 subjects in each of the three primary imaging modes (LSO, SLO, OCT) are shown in FIG. 8. The LSO image provides a 33 deg. wide field view of the retina. The 2-deg. SLO images were taken near the fovea. Cone photoreceptors can be resolved to within ~0.5 deg. (100-150 μm) of the fovea. The cross-sectional OCT image spans 2 mm (6.9 deg.) centered on the fovea. The OCT images are composites of between 5 and 10 frames after flattening and alignment. Ten major retinal layers (nerve fiber, ganglion cell, inner plexiform, inner nuclear, outer plexiform, outer nuclear, inner segments, outer segments, retinal pigment epithelium, choriocapillaris) can be resolved.

Figure 9:
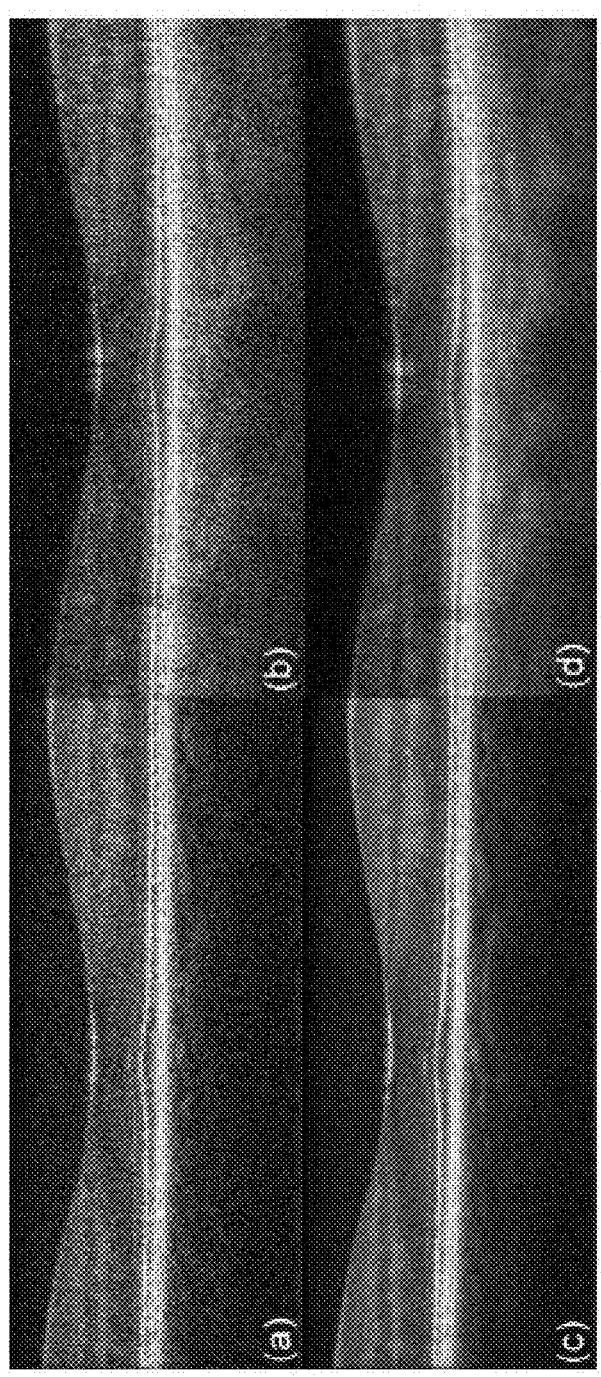
FIG. 9 shows single and 4-frame average cross-sectional FDOCT images through the fovea for one subject that was imaged with both an 850-nm spectrometer-based instrument and the current 1050-nm swept source-based AO-FDOCT imager.

FIG. 9 shows single and 4-frame average cross-sectional FDOCT images through the fovea for one subject that was imaged with both an 850-nm spectrometer-based instrument and the current 1050-nm swept source-based AO-FDOCT imager. Although the axial resolution in the former was better (theoretical axial resolution: 3.6 μm vs. 4.6 μm), the improved penetration into the choroid is clear.

Figure 10:
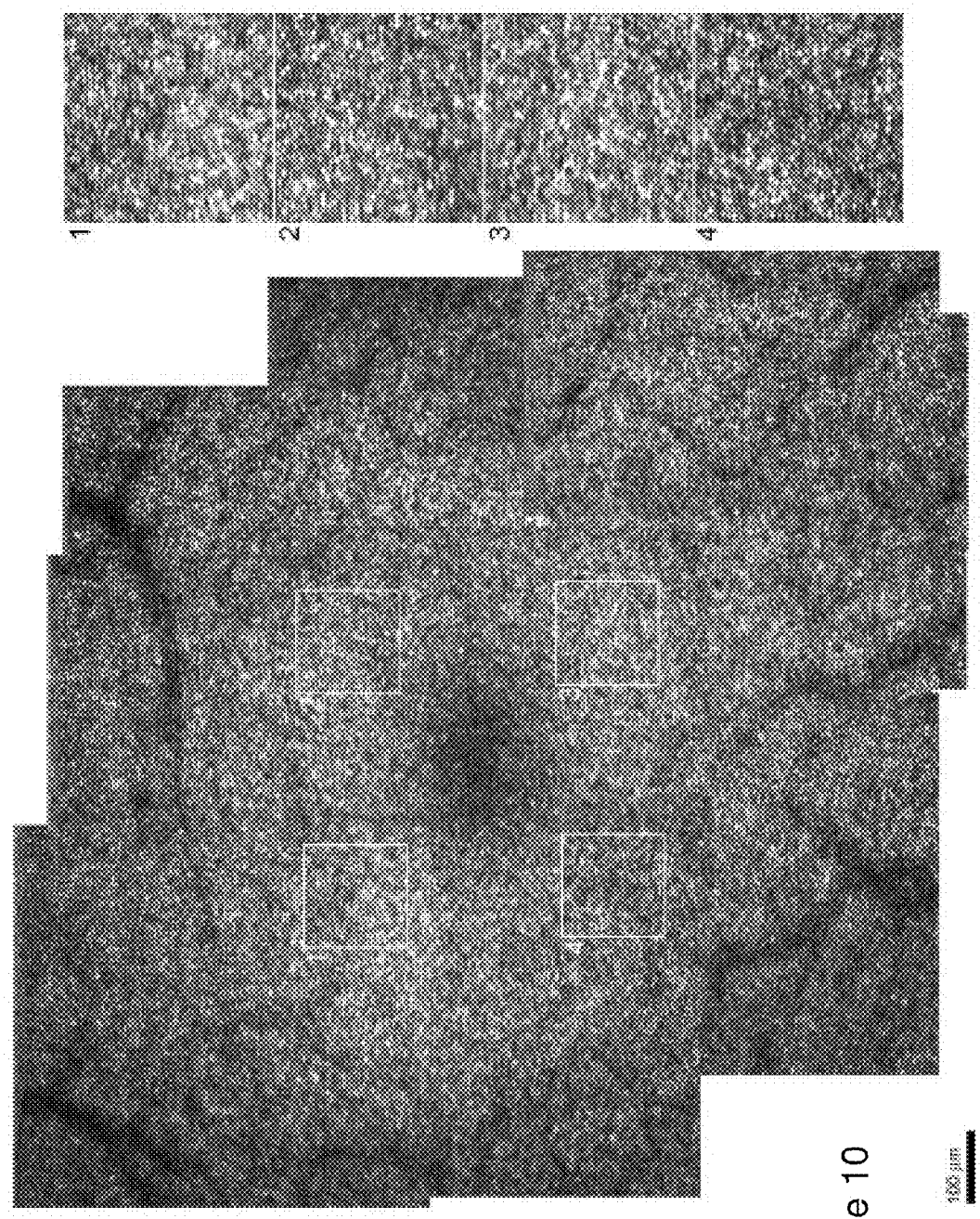
FIG. 10 shows an AOSLO montage in the central ~3 deg. for one subject.

An AOSLO montage in the central ~3 deg. for one subject is shown in FIG. 10. The montage was created by stitching together a 3×3 matrix of 2-deg. AOSLO images. The magnified regions to the right indicate excellent cone contrast within 0.5 deg. (~150 μm) of the fovea center. For imaging larger retinal patches, strip scan and strip montage image scanning procedures can be used to map structures (e.g., photoreceptors) across the macula or retinal region.

A montage or mosaic image can be created using a scanning device of the imaging apparatus (e.g., the third scanning device 38 shown in FIG. 1 or a scanner 220 shown in FIG. 3). For example, the scanning device includes a scanner and a driver. The scanner can be a resonant scanner that scans a first portion of the eye (e.g., a first portion of the retina) and the driver can be a galvanometer that repositions the resonant scanner on a second portion of the eye (e.g., a second portion of the retina) according to a predetermined off-set. Thus, a first image (e.g., image) can be acquired by the imaging apparatus when the resonant scanner scans the imaging beam along on the first portion of the eye. The scan can be a raster scan or a two-dimensional transverse scan. A second image (e.g., image) can be acquired by the imaging apparatus after the galvanometer repositions the scanner on the second portion of the eye. The process can be repeated to acquire images over the other portions of the eye until the montage has been generated. An exemplary procedure for recording montage or mosaic images is described in U.S. Pat. No. 7,758,189, the disclosure of which is herein incorporated by reference in its entirety.

Figure 11:
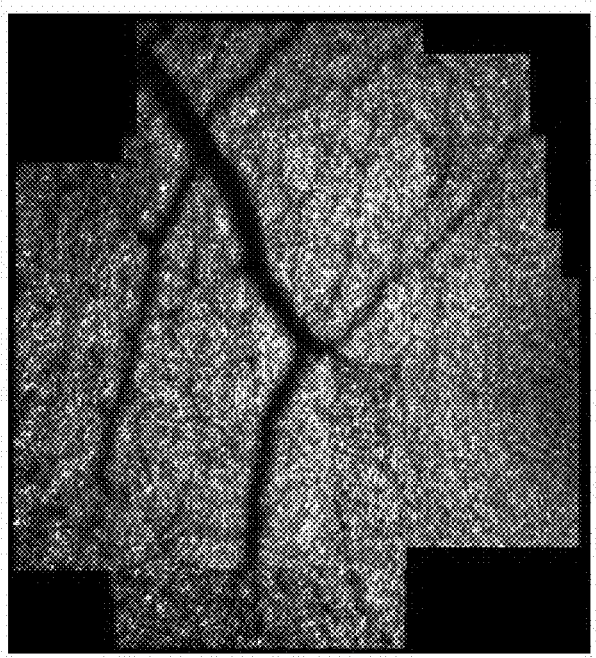
FIG. 11 shows the results compared to no registration and registration frame-by-frame.

The automated registration algorithm co-aligns multiple frames for averaging (to increase SNR), for quantification of large retinal patches in the presence of intra-frame warping, to determine the shift in a secondary imaging mode where SNR is extremely low (i.e., fluorescence), or as a precursor to stitching montages or strips together. When aligning a stack of frames from a single fixation point, the algorithm aligns by horizontal strips 10 pixels wide. This makes the registered image more impervious to torsional eye motion that can cause intra-frame warping. As a demonstration of the algorithm capabilities, a stack of AOSLO images taken for the challenging case of high image uniformity (and lack of high contrast vessel targets) in the foveal avascular zone were aligned. FIG. 11 shows the results compared to no registration and registration frame-by-frame.

Figure 12:
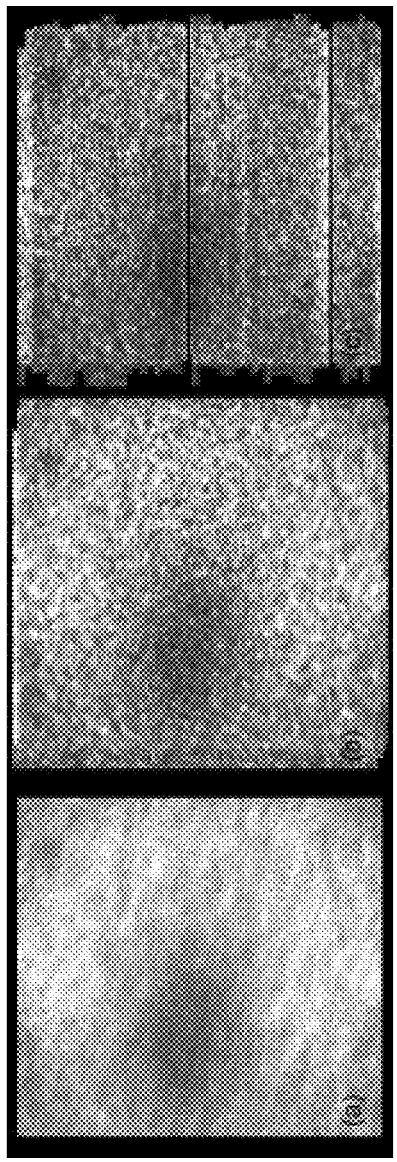
FIG. 12 shows a registered stack of multimodal AO images from a slow strip scan in the presence of above average eye movements (for a control subject).

For auto-stitching, our algorithm selects a key frame in a stack, uses the scale invariant feature transform (SIFT) to match frames, and then aligns to the key frames. FIG. 12 shows a registered stack of multimodal AO images from a slow strip scan in the presence of above average eye movements (for a control subject).

Figure 13:
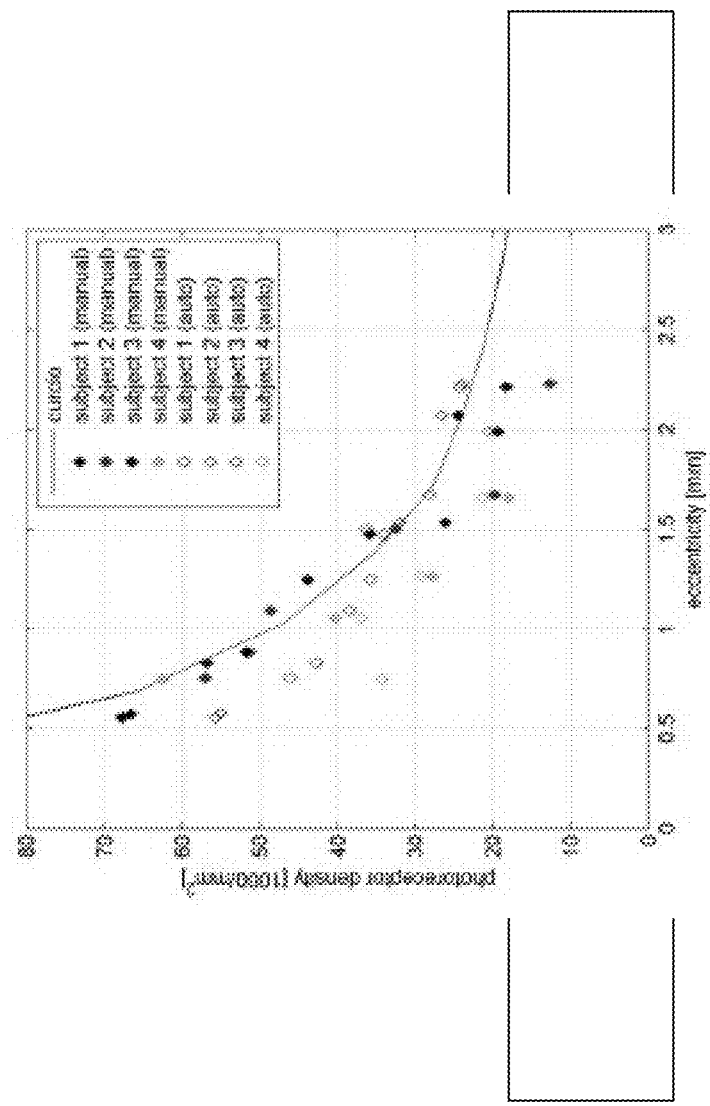
FIG. 13 shows cone photoreceptor counts on several retinal patches at various eccentricity from a single 2-deg. AOSLO scan near the fovea (identifiable in the images) for 4 subjects using manual and automated methods.

Cone photoreceptor counts were performed on several retinal patches at various eccentricity from a single 2-deg. AOSLO scan near the fovea (identifiable in the images) for 4 subjects using manual and automated methods (FIG. 13). The automated cone photoreceptor counting algorithm corrects for a non-uniform image background, applies morphological operators, and uses a centroiding algorithm for initial identification of cone locations. The locations are then filtered to provide a final cone count in the retinal patch examined. The final filter parameter is set according to the eccentricity and so requires some limited user input. The manual (solid symbols) and automated (open symbols) results are compared to previously reported histology. In general, the automated result showed good correspondence with the manual counts and histology. For lower eccentricities close to the resolution limit of the instrument, the algorithm begins to break down and underestimate the count.

Figure 14:
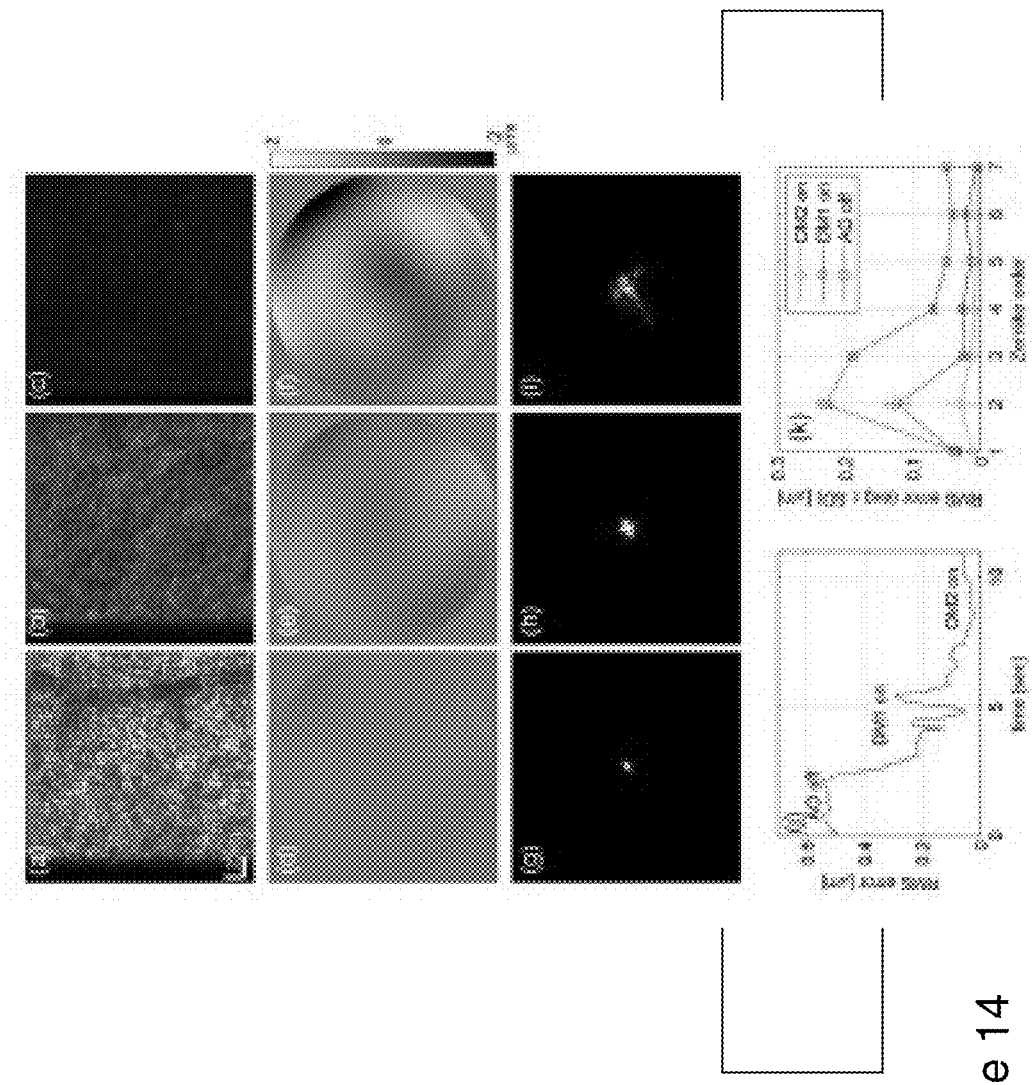
FIG. 14 shows an example of the AO performance achieved in one human subject.

FIG. 14 shows an example of the AO performance achieved in one human subject. Three images are shown: SLO (1 deg. field, top row), WS (second row), and PSF (third row) for three cases: no AO correction (third column), static DM1 (woofer) correction (second column), and dual-DM correction (first column) with both static DM1 (woofer) and dynamic DM2 (tweeter). The time course of the correction and the aberrations broken down by Zernike order are also shown. Both mirrors are important to achieve the best possible AO correction in human subjects.

The multimodal AO system can be configured to acquire images from the SLO and OCT channels sequentially while the LSO, AO, HS-WS, and RT are all running continuously. This can be done in a unique configuration whereby the real time OCT processing board that drives the galvos can accept input from either the SLO RS or the OCT swept source. Thus the multiple scanning schemes available for both modes (OCT line and raster, SLO raster, montages, strip scans, etc.) use all the same hardware (scanners, real time processing board) and are set up from an extremely intuitive and flexible user interface. Another multimodal AO retinal imaging system can include simultaneous SLO and OCT imaging, but it uses a spectrometer-based FDOCT channel. Thus, for some applications that target deeper structures and vasculature, the enhanced depth penetration with 1-µm illumination takes precedence over simultaneous OCT/SLO imaging.

A suite of post-processing analysis routines for both SLO and OCT images have been developed. The functionality of these algorithms include registration, image averaging, montage and strip stitching, photoreceptor quantification, photoreceptor density mapping, and segmentation (retinal layer and drusen). Some algorithms require limited user input (i.e., are semi-automated) while others operate in a fully automated manner (e.g., photoreceptor counting). With the multimodal image acquisition modes and these analysis tools, it is now possible to fully map retinal layers and critical structures across the entire macula.

Figure 15:
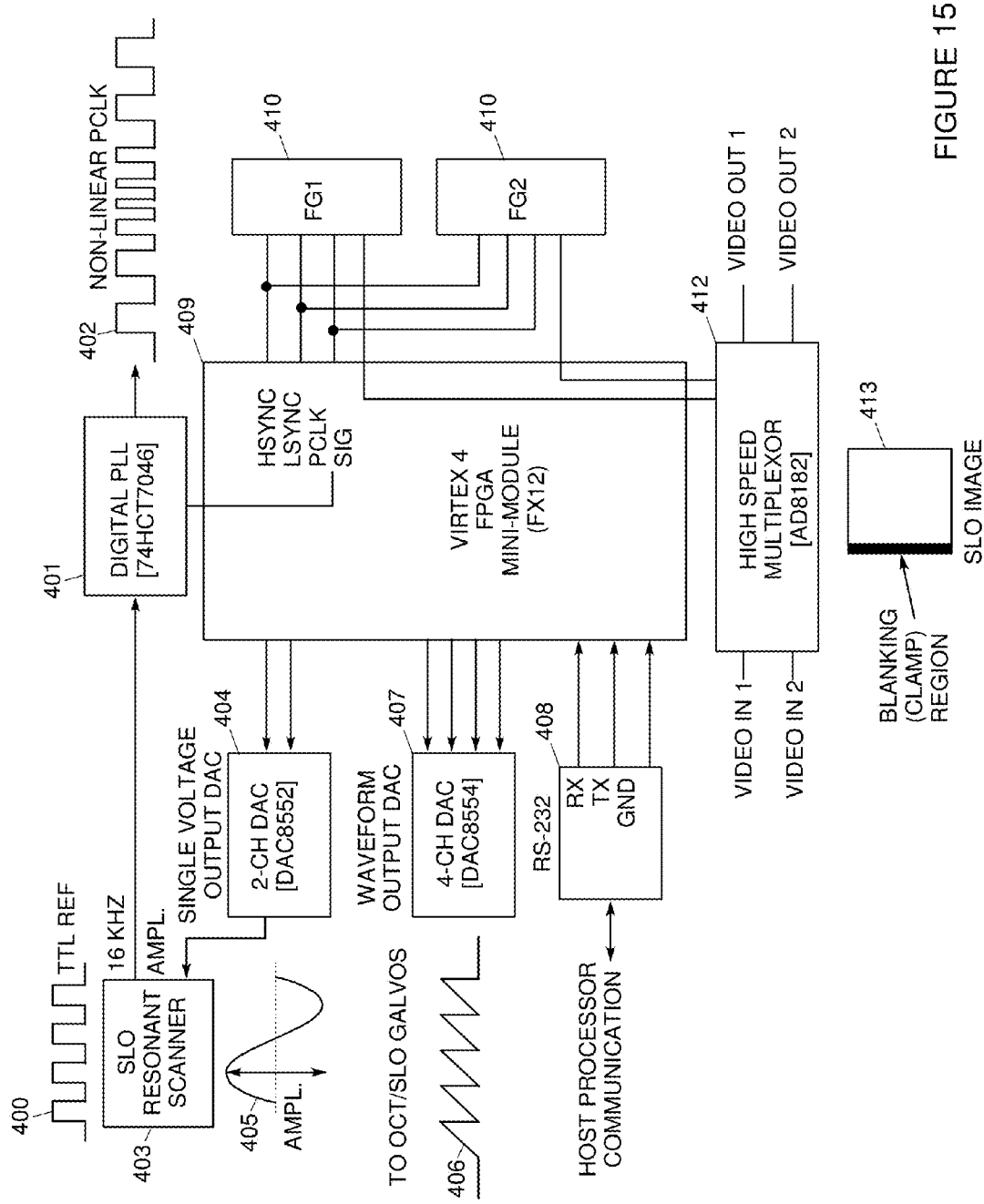
FIG. 15 shows an exemplary SLO timing board functional schematic.

FIG. 15 shows an exemplary SLO timing board functional schematic. The SLO timing board can include a FPGA-based design to provide further device automation and enhanced performance (e.g., increase SNR from a stable blanking region). The functionality of the timing board can include generation of a non-linear pixel clock for automatic SLO image dewarping, automatic electronic video blanking via high speed analog signal multiplexing, generation of SLO/OCT waveforms and offsets (user-controlled), generation of the SLO resonant scanner amplitude control signal (user-controlled), and/or dual channel video operation that can be coupled to simultaneous reflectance/fluorescence imaging. The SLO timing board includes a TTL reference signal 400, a digital PLL chip 401, a non-linear pixel clock signal 402, a resonant scanner driver 403, a two-channel digital-to-analog converter 404, an RS drive signal 405, an OCT/SLO scanner drive waveforms 406, a four-channel digital-to-analog converter 407, a RS-232 port for host computer communication 408, a field programmable gated array chip 409, framegrabber ports 410, a high speed video multiplexor 412, and a SLO image showing blanking region 413.

The above-described techniques can be implemented in digital electronic circuitry, or in computer hardware, firmware, software, or in combinations of them. The implementation can be as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps can be performed by one or more programmable processors executing a computer program to perform functions of the technology by operating on input data and generating output. Method steps can also be performed by, and apparatus can be implemented as, special purpose logic circuitry, e.g., a FPGA (field programmable gate array), a FPAA (field-programmable analog array), a CPLD (complex programmable logic device), a PSoC (Programmable System-on-Chip), ASIP (application-specific instruction-set processor), or an ASIC (application-specific integrated circuit), or the like. Subroutines can refer to portions of the stored computer program and/or the processor, and/or the special circuitry that implement one or more functions.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Data transmission and instructions can also occur over a communications network. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

The terms "module" and "function," as used herein, mean, but are not limited to, a software or hardware component which performs certain tasks. A module may advantageously be configured to reside on addressable storage medium and configured to execute on one or more processors. A module may be fully or partially implemented with a general purpose integrated circuit (IC), DSP, FPGA or ASIC. Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules. Additionally, the components and modules may advantageously be implemented on many different platforms, including computers, computer servers, data communications infrastructure equipment such as application-enabled switches or routers, or telecommunications infrastructure equipment, such as public or private telephone switches or private branch exchanges (PBX). In any of these cases, implementation may be achieved either by writing applications that are native to the chosen platform, or by interfacing the platform to one or more external application engines.

To provide for interaction with a user, the above described techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The above described techniques can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an example implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet, and include both wired and wireless networks. Communication networks can also all or a portion of the PSTN, for example, a portion owned by a specific carrier.

The computing system can include clients and servers. A client and server are generally remote from each other and typically interact through a communication network. The relationship of client and server arises by virtue of computer programs running on the respective computers and having a client-server relationship to each other.

While the invention has been particularly shown and described with reference to specific illustrative embodiments, it should be understood that various changes in form and detail may be made without departing from the spirit and scope of the invention.

What is claimed is:

1. An optical apparatus comprising:
    a system of optical components capable of operating in a scanning laser ophthalmoscope (SLO) mode and an optical coherence tomography (OCT) mode, the system of optical components including:
    a first optical module for the SLO mode including:
        a first source adapted to provide a first imaging beam for the SLO mode;
        a first detection device configured to receive a first signal associated with a first image of a retina of an eye;
    a second optical module for the OCT mode including:
        a second source adapted to provide a second imaging beam for the OCT mode;
        a second detection device configured to receive a second signal associated with a second image of the retina;
    a first scanning device configured (i) to move the first imaging beam along the retina in the slow axis of the SLO mode to acquire the first image and (ii) to move the second imaging beam along the retina in the fast axis of the OCT mode to acquire the second image;
    a second scanning device configured to move the first imaging beam along the retina in the fast axis of the SLO mode to acquire the first image; and
    a third scanning device configured to move the second imaging beam along the retina in the slow axis of the OCT mode to acquire the second image.

2. The apparatus of claim 1 wherein the first scanning device, the second scanning device and the third scanning device are positioned at pupil conjugates in the system of optical components.

3. The apparatus of claim 1 wherein the first scanning device is mounted to the third scanning device at a pupil conjugate.

4. The apparatus of claim 1 wherein the second imaging beam of the OCT mode is introduced by a beamsplitter positioned between the eye and the SLO module.

5. The apparatus of claim 4 further comprising a first wavefront compensator and a second wavefront compensator positioned between the beamsplitter and the eye.

6. The apparatus of claim 1 wherein system of optical components are adapted to simultaneously image the same retinal coordinates in the SLO mode and OCT mode.

7. The apparatus of claim 1 wherein the third scanning device is configured to scan the first imaging beam to generate a mosaic image of the eye.

8. An optical apparatus comprising:
    a system of optical components capable of operating in a scanning laser ophthalmoscope (SLO) mode and an optical coherence tomography (OCT) mode, the system of optical components including:

a first optical module for the SLO mode including:
a first source adapted to provide a first imaging beam for the SLO mode;
a first detection device configured to receive a first signal associated with a first image of a retina of an eye;
a second optical module for the OCT mode including:
a second source adapted to provide a second imaging beam for the OCT mode;
a second detection device configured to receive a second signal associated with a second image of the retina;
a first scanning device configured (i) to move the first imaging beam along the retina in the slow axis of the SLO mode to acquire the first image and (ii) to move the second imaging beam along the retina in the fast axis of the OCT mode to acquire the second image; and
a third optical module configured to (i) detect an optical distortion and (ii) correct the optical distortion in at least one of the first or second imaging beams scanned on the eye.

9. The apparatus of claim 8 wherein the third optical module comprises:
a wavefront sensor adapted to detect the optical distortion; and
a wavefront compensator adapted to correct the optical distortion in the first or second imaging beam.

10. An optical apparatus comprising:
a system of optical components capable of operating in a scanning laser ophthalmoscope (SLO) mode and an optical coherence tomography (OCT) mode, the system of optical components including:
a first optical module for the SLO mode including:
a first source adapted to provide a first imaging beam for the SLO mode;
a first detection device configured to receive a first signal associated with a first image of a retina of an eye;
a second optical module for the OCT mode including:
a second source adapted to provide a second imaging beam for the OCT mode;
a second detection device configured to receive a second signal associated with a second image of the retina;
a first scanning device configured (i) to move the first imaging beam along the retina in the slow axis of the SLO mode to acquire the first image and (ii) to move the second imaging beam along the retina in the fast axis of the OCT mode to acquire the second image; and
a fourth optical module configured to operate in a line scanning ophthalmoscope (LSO) mode, the fourth optical module including:
a third source adapted to provide a third imaging beam in a line focus configuration for the LSO mode, wherein the fourth optical module is configured to (i) scan the third imaging beam in the line focus configuration along the retina in a second dimension and (ii) descan the second light returning from the eye in the second dimension, the light returning from the eye directed to a third detection device.

11. An optical apparatus comprising:
a system of optical components capable of operating in a scanning laser ophthalmoscope (SLO) mode and an optical coherence tomography (OCT) mode, the system of optical components including:
a first optical module for the SLO mode including:
a first source adapted to provide a first imaging beam for the SLO mode;
a first detection device configured to receive a first signal associated with a first image of a retina of an eye;
a second optical module for the OCT mode including:
a second source adapted to provide a second imaging beam for the OCT mode;
a second detection device configured to receive a second signal associated with a second image of the retina;
a first scanning device configured (i) to move the first imaging beam along the retina in the slow axis of the SLO mode to acquire the first image and (ii) to move the second imaging beam along the retina in the fast axis of the OCT mode to acquire the second image; and
a fifth optical module adapted to track a reference feature of the retina of the eye, the first optical module adapted to control the position of the first imaging beam relative to the reference feature to correct for motion of the eye.

12. An optical apparatus comprising:
a system of optical components capable of operating in a scanning laser ophthalmoscope (SLO) mode and an optical coherence tomography (OCT) mode, the system of optical components including:
a first optical module for the SLO mode including:
a first source adapted to provide a first imaging beam for the SLO mode;
a first detection device configured to receive a first signal associated with a first image of a retina of an eye;
a second optical module for the OCT mode including:
a second source adapted to provide a second imaging beam for the OCT mode;
a second detection device configured to receive a second signal associated with a second image of the retina;
a first scanning device configured (i) to move the first imaging beam along the retina in the slow axis of the SLO mode to acquire the first image and (ii) to move the second imaging beam along the retina in the fast axis of the OCT mode to acquire the second image; and
a sixth optical module adapted to provide a fluorescence imaging channel.

13. An optical apparatus comprising:
a system of optical components capable of operating in a scanning laser ophthalmoscope (SLO) mode and an optical coherence tomography (OCT) mode, the system of optical components including:
a first optical module for the SLO mode including:
a first source adapted to provide a first imaging beam for the SLO mode;
a first detection device configured to receive a first signal associated with a first image of a retina of an eye;
a second optical module for the OCT mode including:
a second source adapted to provide a second imaging beam for the OCT mode;
a second detection device configured to receive a second signal associated with a second image of the retina;
a first scanning device configured (i) to move the first imaging beam along the retina in the slow axis of the SLO mode to acquire the first image and (ii) to move the second imaging beam along the retina in the fast axis of the OCT mode to acquire the second image; and wherein the OCT mode can include a Fourier domain OCT channel configured to be spectrometer-based or swept source-based.

14. An optical apparatus comprising:
a system of optical components capable of operating in a scanning laser ophthalmoscope (SLO) mode and an optical coherence tomography (OCT) mode, the system of optical components including:
a first optical module for the SLO mode including:
a first source adapted to provide a first imaging beam for the SLO mode;
a first detection device configured to receive a first signal associated with a first image of a retina of an eye,
a second optical module for the OCT mode including:
a second source adapted to provide a second imaging beam for the OCT mode;
a second detection device configured to receive a second signal associated with a second image of the retina;
a first scanning device configured (i) to move the first imaging beam along the retina in the slow axis of the SLO mode to acquire the first image and (ii) to move the second imaging beam along the retina in the fast axis of the OCT mode to acquire the second image; and
wherein the system of optical components further comprises at least two spherical mirrors, each having a diameter greater than 20 cm, positioned relative to the eye and configured to provide a field of view greater than 30 degrees.

15. An optical apparatus comprising:
a system of optical components capable of operating in a scanning laser ophthalmoscope (SLO) mode and an optical coherence tomography (OCT) mode, the system of optical components including:
a first optical module for the SLO mode including:
a first source adapted to provide a first imaging beam for the SLO mode;
a first detection device configured to receive a first signal associated with a first image of a retina of an eye;
a second optical module for the OCT mode including:
a second source adapted to provide a second imaging beam for the OCT mode;
a second detection device configured to receive a second signal associated with a second image of the retina;
a first scanning device configured (i) to move the first imaging beam along the retina in the slow axis of the SLO mode to acquire the first image and (ii) to move the second imaging beam along the retina in the fast axis of the OCT mode to acquire the second image; and
wherein the wavelength of the second imaging beam of the OCT mode is selected to match a physical property of the tissue.

16. A method of imaging a retina of an eye, comprising:
acquiring a SLO image of the eye by receiving, on a first detector, a first light returning from the eye and providing a first electrical signal responsive to the first light at each of a plurality of locations along the first detector, the first electrical signal indicative of the SLO image of the eye;
acquiring an OCT image of the eye by receiving, on a second detector, a second light returning from the eye and providing a second electrical signal responsive to the second light at each of a plurality of locations along the second detector, the second electrical signal combined with a reference signal from a reference arm, the second electrical signal and the reference signal associated with the OCT image of the eye; and
scanning, using a first scanning device, (i) a first imaging beam along the retina in the slow axis of the SLO mode to acquire the SLO image and (ii) a second imaging beam along the retina in the fast axis of the OCT mode to acquire the OCT image.

17. The method of claim 16 further comprising:
scanning, using a second scanning device, the first imaging beam along the retina in the fast axis of the SLO mode to acquire the SLO image; and
scanning, using a third scanning device, the second imaging beam along the retina in the slow axis of the OCT mode to acquire the OCT image.

18. The method of claim 16 further comprising introducing, using a beamsplitter, the second imaging beam of the OCT mode between the eye and the SLO mode.

19. The method of claim 16 further comprising simultaneously imaging the same retinal coordinates in the SLO mode and OCT mode.

20. The method of claim 16 further comprising:
detecting an optical distortion; and
correcting the optical distortion in at least one of the first or second imaging beams scanned on the eye.

21. The method of claim 16 further comprising acquiring a LSO image of the eye by receiving, on a one-dimensional detector, a third light returning from the eye and providing a third electrical signal responsive to the third light at each of a plurality of locations along the one-dimensional detector, the second electrical signal indicative of the LSO image of the eye.

22. The method of claim 16 further comprising:
tracking a reference feature of the retina of the eye; and
controlling the position of the first imaging beam relative to the reference feature to correct for motion of the eye.

23. The method of claim 16 further comprising providing simultaneous, high-fidelity, wide dynamic range correction of lower- and higher-order ocular aberrations using a dual-deformable mirror configuration.

24. The method of claim 16 further comprising imaging a field of view greater than 30 degrees using at least two spherical mirrors, each having a diameter greater than 20 em, positioned relative to the eye.

25. An optical apparatus comprising:
a system of optical components capable of operating in a scanning laser ophthalmoscope (SLO) mode and an optical coherence tomography (OCT) mode, the system of optical components including:
at least two spherical mirrors, each having a diameter greater than 20 em, positioned relative to the eye;
at least two deformable mirrors positioned behind the at least two spherical mirrors;
a beamsplitter positioned behind the at least two deformable mirrors;
an OCT optical module introduced by the beamsplitter;
a SLO optical module behind the beamsplitter;
a first scanning device positioned between the beamsplitter and the eye, the first scanning device configured (i) to move a first imaging beam along the retina in the slow axis of the SLO mode to acquire an SLO image and (ii) to move a second imaging beam along the retina in the fast axis of the OCT mode to acquire an OCT image;
a second scanning device positioned behind the beamsplitter, the second scanning device configured to move the first imaging beam along the retina in the fast axis of the SLO mode to acquire the SLO image; and a third scanning device positioned between the beamsplitter and the eye, the third scanning device configured to move the second imaging beam along the retina in the slow axis of the OCT mode to acquire the OCT image.

26. The apparatus of claim 25 wherein the at least two deformable mirrors, the first scanning device, the second scanning device and the third scanning device are positioned at pupil conjugates in the system of optical components.

* * * * *